United States Patent
Tran et al.

(10) Patent No.: US 7,037,656 B2
(45) Date of Patent: May 2, 2006

(54) METHODS AND COMPOSITIONS FOR IDENTIFYING LIGANDS FOR NUCLEAR RECEPTORS

(75) Inventors: Hiep Tuan Tran, West Chester, PA (US); Salam Shaaban, Oxford (GB); Hossein Askari, West Chester, PA (US); Michael Schwartz, Riverton, NJ (US); Tauseef Butt, Audubon, PA (US)

(73) Assignee: Lifesensors, Inc., Malvern, PA (US)

( * ) Notice: Subject to any disclaimer, the term of this patent is extended or adjusted under 35 U.S.C. 154(b) by 429 days.

(21) Appl. No.: 10/204,169

(22) PCT Filed: Feb. 20, 2001

(86) PCT No.: PCT/US01/05429

§ 371 (c)(1),
(2), (4) Date: Dec. 2, 2002

(87) PCT Pub. No.: WO01/61350

PCT Pub. Date: Aug. 23, 2001

(65) Prior Publication Data

US 2003/0211455 A1    Nov. 13, 2003

Related U.S. Application Data

(60) Provisional application No. 60/183,193, filed on Feb. 18, 2000.

(51) Int. Cl.
  *C12Q 1/68* (2006.01)
(52) U.S. Cl. ........................................ 435/6; 435/320.1
(58) Field of Classification Search .................... 435/6, 435/320.1
See application file for complete search history.

(56) References Cited

FOREIGN PATENT DOCUMENTS

WO    WO 97/45737    12/1997

OTHER PUBLICATIONS

Tran, Hiep T., et al., "Reconstruction of Ligand-Dependent Transactivation of *Choristoneura fumiferana* Ecdysone Receptor in Yeast", Molecular Endocrinology 15(7): 1140-1153 (2001).

Tran, Hiep T., et al., "Requirement of co-factors for the ligand-mediated activity of the insect ecdysteriod receptor in yeast", Journal of Molecular Endocrinology, 27: 191-209 (2001).

Dela Cruz, Fernando, et al., "Drosophila Ecdysone Receptor Functions as a Constitutive Activator in Yeast", J. Steroid Biochem. Molec. Biol. 62(4):353-359 (1997).

Walfish, Paul G., et al., "Yeast hormone response element assays detect and characterize GRIP1 coactivator-dependent activation of transcription by thyroid and retinoid nuclear receptors", Proc. Natl. Acad. Sci. USA 94: 3697-3702 (1997).

*Primary Examiner*—James Ketter
(74) *Attorney, Agent, or Firm*—Dann Dorfman Herrell and Skillman; Kathleen D. Rigaut

(57) ABSTRACT

A yeast-based system and methods of use therefore are provided for identifying new molecules which activate nuclear receptors in a ligand-dependent fashion. In a preferred embodiment, a method is provided utilizing ecdysone receptor, USP and GRIP I encoding expression vectors which may be used to advantage for screening new and useful insecticidal compounds, detecting insecticidal residues as well as to regulate expression of a gene of interest in a host in a ligand-dependent manner.

48 Claims, 18 Drawing Sheets

SEQUENCE LISTING

<160> NUMBER OF SEQ ID NOS: 29

<210> SEQ ID NO 1
<211> LENGTH: 30
<212> TYPE: DNA
<213> ORGANISM: Artificial Sequence
<220> FEATURE:
<223> OTHER INFORMATION: Synthetic Sequence

<400> SEQUENCE: 1
agagacaagg gttcaatgca cttgtccaat                           30

<210> SEQ ID NO 2
<211> LENGTH: 45
<212> TYPE: DNA
<213> ORGANISM: Artificial Sequence
<220> FEATURE:
<223> OTHER INFORMATION: Synthetic Sequence

<400> SEQUENCE: 2
cttgtcttaa gactaagagg tggtatgaag cggcgctggt cgaac          45

<210> SEQ ID NO 3
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 3
tgctgactta ggccatggcc gt                                   22

<210> SEQ ID NO 4
<211> LENGTH: 42
<212> TYPE: DNA
<213> ORGANISM: Artificial Sequence
<220> FEATURE:
<223> OTHER INFORMATION: Synthetic Sequence

<400> SEQUENCE: 4
ttgtcttaag actaagaggt ggtatggaca actgcgacca gg             42

<210> SEQ ID NO 5
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 5
agcaggtgga ccatggacat gg                                   22

<210> SEQ ID NO 6
<211> LENGTH: 68
<212> TYPE: DNA
<213> ORGANISM: Artificial Sequence
<220> FEATURE:
<223> OTHER INFORMATION: Synthetic Sequence

<400> SEQUENCE: 6
aggagtcgac cttacatctt gtcttaagac taagaggtgg tatgtatccg cctaaccatc    60
cgctgagc                                                   68

<210> SEQ ID NO 7
<211> LENGTH: 30
<212> TYPE: DNA
<213> ORGANISM: Artificial Sequence
<220> FEATURE:
<223> OTHER INFORMATION: Synthetic Sequence

<400> SEQUENCE: 7
aaggacgcgt cttttcggtt agagcggatg                           30

<210> SEQ ID NO 8

```
<211> LENGTH: 70
<212> TYPE: DNA
<213> ORGANISM: Artificial Sequence
<220> FEATURE:
<223> OTHER INFORMATION: Synthetic Sequence

<400> SEQUENCE: 8
aggagtcgac cttacatctt gtcttaagac taagaggtgg tatggacctg aaacacgaag     60
tggcttaccg                                                            70

<210> SEQ ID NO 9
<211> LENGTH: 27
<212> TYPE: DNA
<213> ORGANISM: Artificial Sequence
<220> FEATURE:
<223> OTHER INFORMATION: Synthetic Sequence

<400> SEQUENCE: 9
aagggagctc taatctcccg cgcattc                                         27

<210> SEQ ID NO 10
<211> LENGTH: 68
<212> TYPE: DNA
<213> ORGANISM: Artificial Sequence
<220> FEATURE:
<223> OTHER INFORMATION: Synthetic Sequence

<400> SEQUENCE: 10
aggagtcgac cttacatctt gtcttaagac taagaggtgg tatgcggcag caggaggaac     60
tgtgtctg                                                              68

<210> SEQ ID NO 11
<211> LENGTH: 27
<212> TYPE: DNA
<213> ORGANISM: Artificial Sequence
<220> FEATURE:
<223> OTHER INFORMATION: Synthetic Sequence

<400> SEQUENCE: 11
aagggagctc taatctcccg cgcattc                                         27

<210> SEQ ID NO 12
<211> LENGTH: 59
<212> TYPE: DNA
<213> ORGANISM: Artificial Sequence
<220> FEATURE:
<223> OTHER INFORMATION: Synthetic Sequence

<400> SEQUENCE: 12
aggagtcgac cttacatctt gtcttaagac taagaggtgg tatgtcaagt gtggcgaag      59

<210> SEQ ID NO 13
<211> LENGTH: 30
<212> TYPE: DNA
<213> ORGANISM: Artificial Sequence
<220> FEATURE:
<223> OTHER INFORMATION: Synthetic Sequence

<400> SEQUENCE: 13
ccttccatgg gaatgtcaat aatgcccgtg                                      30

<210> SEQ ID NO 14
<211> LENGTH: 68
<212> TYPE: DNA
<213> ORGANISM: Artificial Sequence
```

```
<220> FEATURE:
<223> OTHER INFORMATION: Synthetic Sequence

<400> SEQUENCE: 14
aggagtcgac cttacatctt gtcttaagac taagaggtgg tatgtacccg cctaatcacc    60
ccctgagt                                                              68

<210> SEQ ID NO 15
<211> LENGTH: 30
<212> TYPE: DNA
<213> ORGANISM: Artificial Sequence
<220> FEATURE:
<223> OTHER INFORMATION: Synthetic Sequence

<400> SEQUENCE: 15
ccttccatgg gaatgtcaat aatgcccgtg                                      30

<210> SEQ ID NO 16
<211> LENGTH: 62
<212> TYPE: DNA
<213> ORGANISM: Artificial Sequence
<220> FEATURE:
<223> OTHER INFORMATION: Synthetic Sequence

<400> SEQUENCE: 16
aggagtcgac cttacatctt gtcttaagac taagaggtgg tatgatgaaa agaagatggt    60
cc                                                                    62

<210> SEQ ID NO 17
<211> LENGTH: 30
<212> TYPE: DNA
<213> ORGANISM: Artificial Sequence
<220> FEATURE:
<223> OTHER INFORMATION: Synthetic Sequence

<400> SEQUENCE: 17
aaggacgcgt tgaacagaat gtcgtccgct                                      30

<210> SEQ ID NO 18
<211> LENGTH: 68
<212> TYPE: DNA
<213> ORGANISM: Artificial Sequence
<220> FEATURE:
<223> OTHER INFORMATION: Synthetic Sequence

<400> SEQUENCE: 18
aggagtcgac cttacatctt gtcttaagac taagaggtgg tatgcggcag caggaggaac    60
tgtgtctg                                                              68

<210> SEQ ID NO 19
<211> LENGTH: 30
<212> TYPE: DNA
<213> ORGANISM: Artificial Sequence
<220> FEATURE:
<223> OTHER INFORMATION: Synthetic Sequence

<400> SEQUENCE: 19
aaggacgcgt tgaacagaat gtcgtccgct                                      30

<210> SEQ ID NO 20
<211> LENGTH: 61
<212> TYPE: DNA
<213> ORGANISM: Artificial Sequence
<220> FEATURE:
```

-continued

<223> OTHER INFORMATION: Synthetic Sequence

<400> SEQUENCE: 20
aggagtcgac cttacatctt gtcttaagac taagaggtgg tatgctgaag aaggaaaaac    60
c                                                                   61

<210> SEQ ID NO 21
<211> LENGTH: 61
<212> TYPE: DNA
<213> ORGANISM: Artificial Sequence
<220> FEATURE:
<223> OTHER INFORMATION: Synthetic Sequence

<400> SEQUENCE: 21
aggagtcgac cttacatctt gtcttaagac taagaggtgg tatggatccc agcgatcgag    60
g                                                                   61

<210> SEQ ID NO 22
<211> LENGTH: 31
<212> TYPE: DNA
<213> ORGANISM: Artificial Sequence
<220> FEATURE:
<223> OTHER INFORMATION: Synthetic Sequence

<400> SEQUENCE: 22
aaggacgcgt ccacaagttg cttgttctag g                                  31

<210> SEQ ID NO 23
<211> LENGTH: 68
<212> TYPE: DNA
<213> ORGANISM: Artificial Sequence
<220> FEATURE:
<223> OTHER INFORMATION: Synthetic Sequence

<400> SEQUENCE: 23
aggagtcgac cttacatctt gtcttaagac taagaggtgg tatgtatccg ccaaatcatc    60
cgctcagc                                                            68

<210> SEQ ID NO 24
<211> LENGTH: 30
<212> TYPE: DNA
<213> ORGANISM: Artificial Sequence
<220> FEATURE:
<223> OTHER INFORMATION: Synthetic Sequence

<400> SEQUENCE: 24
aaggacgcgt cacaagttgc ttgttctagg                                    30

<210> SEQ ID NO 25
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 25

Val Asn Ser Ser Ile Ser Ser
 1               5

<210> SEQ ID NO 26
<211> LENGTH: 5
<212> TYPE: PRT
<213> ORGANISM: Artificial Sequence
<220> FEATURE:

-continued

```
<223> OTHER INFORMATION: Synthetic Sequence

<400> SEQUENCE: 26

Tyr Pro Pro Asn His
1               5

<210> SEQ ID NO 27
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 27

Arg Gln Gln Glu Glu Leu
1               5

<210> SEQ ID NO 28
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 28

Arg Gln Gln Glu Glu Leu Cys Leu Val
1               5

<210> SEQ ID NO 29
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 29

Arg Gln Gln Glu Glu Leu Cys Val Leu
1               5
```

US 7,037,656 B2

METHODS AND COMPOSITIONS FOR IDENTIFYING LIGANDS FOR NUCLEAR RECEPTORS

This application is a §371 application of PCT/US01/05429, filed Feb. 20, 2001, which in turn claims priority under 35 U. S. C. §119(e) to U.S. Provisional Application No. 60/183,193, filed Feb. 18, 2000, the entire disclosure of which is incorporated by reference herein.

FIELD OF THE INVENTION

The present invention relates to a novel screening method for ecdysone (EcR)/ultraspiracle gene product(USP)receptors using a yeast-based expression system. More specifically, the yeast system disclosed facilitates the screening of agonists and antagonists of the steroid/thyroid receptor superfamily.

BACKGROUND OF THE INVENTION

Various publications or patents may be referenced in this application in order to describe the state of the art to which the invention pertains. Complete citations for these references may be found at the end of the specification. Each of these publications or patents is incorporated by reference herein. The steroid and thyroid hormone superfamily of nuclear receptors in mammals and insects is composed of over 150 known proteins. These receptors fall into at least two functionally distinct categories (Class I and Class II) based on whether they function as homodimers or heterodimers, respectively (4). of the two classes, only the Class II receptors function in the nucleus as heterodimers to effect target gene(s) expression in the presence of hormone. The best studied examples of Class II receptor proteins are Retinoic Acid Receptor (RAR), Vitamin D Receptor (VDR), Thyroid Hormone Receptor (TR) and Retinoid X Receptor (RXR). Upon ligand binding, these receptors bind to the 5' regulatory region of the target gene resulting in transcriptional activation (transactivation) of target genes. Gene expression occurs when the activated receptors and other transcription initiating factors act in concert. All nuclear receptors share a common multi-domain structure. They are divided into six domains that are termed A/B, C, D, E and F domains. These domains have been found to possess the following function: transcription activation function (A/B or AF-1, E or AF-2), a DNA binding (C), a steroid binding and dimerization (E), and a nuclear localization (D). The AF-1 domain is responsible for ligand-independent transcription activation, while the AF-2 domain has ligand-dependent activity. Both of these domains may act independently or in concert. For instance, removal of the AF-1 domain in the estrogen receptor has no effect on 17-estradiol (E2) induction of a reporter construct containing a vitellogenin estrogen response element (ERE), whereas the same AF-1 deficient ER demonstrates only 20% of wild-type induction of a pS2-ERE responsive element (18). Estrogen receptor studies using AF-1 and AF-2 truncated ER have demonstrated that AF-1 responds to growth factors that act via second messengers such as cAMP, whereas AF-2 is E2 ligand dependent (9). For the insect ecdysone receptor, removal of AF-1 domain of spruce budworm EcR did not affect either DNA or ligand binding activity of the EcR/USP heterodimer (14). In addition to the Class II receptor proteins found in mammals as described above, ecdysone receptor has been identified in *Drosophila melanogaster* (DmEcR), *Bombyx mori* (BmEcR), *Manduca sexta* (MsEcR), *Chironomus tentans* (CtEcR), *Choristoneura fumiferana* (CfEcR), and from mosquito *Aedes aegypti* (AaEcR) (See review in (12)). The ecdysone receptor (EcR) binds the steroid hormone 20-hydroxyecdysone and, when heterodimerized with the product of the ultraspiracle gene (USP), transactivates target gene expression. It has also been shown that EcR/USP heterodimerization is required for both DNA binding (20) and ligand binding (21), (13) in *D. melanogaster* and *C. fumiferana*. Additional chemical ligands besides 20-hydroxyecdysone, such as other hormone agonists, will also bind to these receptors and cause transactivation of a target gene. To date, the insect USP receptors have been cloned from *D. melanogaster* (DmUSP), *B. mori* (BmUSP), *M. sexta* (MsUSP), *A. aegypti* (AaUSP), and *C. fumiferana* (CfUSP) (See review in (13)). Mammalian retinoid X receptors (RXR) are homologues of insect USP. It has been shown that mammalian RXRs are capable of substituting for USP to form heterodimers with insect EcRs (19, 20; 21 and 22).

Ligand dependent transactivation systems have been reconstructed in yeast for mammalian receptors such as estrogen, thyroid hormone, androgen receptor etc. The coactivators such as GRIP1 and RIP140 have been used to enhance ligand dependent transactivation in yeast for thyroid hormone (Paul Walfish et al., (1997) PNAS 94:3697–3702) and estrogen receptor. Despite the fact that ligand dependent transactivation for series of mammalian nuclear receptors have been successfully reconstructed in the yeast, to date a ligand dependent system was not available for studying insect ecdysone receptors. Others have observed that transcription of reporter genes in the presence of ecdysone receptor expressed in the yeast is constitutive (De la Cruz and Mak, 1997).

One goal of the insecticide industry is the development of safe chemicals which are not only effective but also pest selective. It is an object of the present invention to provide a unique, yeast-based, ligand-mediated transactivation system to facilitate screening of new pesticide chemicals as well as to validate and improve upon potentially valuable insecticidal candidates.

SUMMARY OF THE INVENTION

A yeast-based screening method and system for identifying ligands of nuclear receptors in general and the EcR:USP or EcR:RXR receptors in particular is disclosed herein. Also provided are yeast based expression vectors which may be used to advantage in the screening methods of the present invention.

In one embodiment of the invention, a ligand dependent transactivation system for screening and detecting insecticidal compounds is provided. An exemplary system of the invention comprises a first DNA construct having a nucleic acid molecule encoding an altered ecdysone receptor operably linked to a promoter; a second DNA construct having a nucleic acid molecule encoding a receptor which heterodimerizes with the altered ecdysone receptor for transactivation, this nucleic acid molecule being operably linked to a promoter; a third DNA construct comprising a promoter containing a plurality of ecdysone response elements, the promoter being operably linked to a reporter gene or a gene of interest for expression; a fourth DNA construct encoding a co-activator molecule, the co-activator molecule being operably linked to a promoter sequence; and a host cell comprising the first, second, third and fourth DNA constructs, expression of the reporter gene being dependent upon ligand-dependent co-activation of the ecdysone receptor effectuated by the insecticidal compound.

In the ligand dependent transactivation system of the invention, the second DNA construct encodes a receptor selected from the group consisting of insect USP or mammalian retinoid X receptors including USP a form, USP b form, ΔA/B USP and retinoid X receptor α, retinoid X receptor β and retinoid receptor γ. The co-activator molecule is a molecule that interact with EcR/USP or EcR/RXR complex including, without limitation, coactivators from the SRC-coactivator family such as GRIP 1, SRC1 and p/CIP. At least one of the promoters operably linked to the DNA constructs described may be an inducible promoter selected from the group consisting of CUP1, HSP70, galactose-inducible promoters such as GAL1, GAL10. Alternatively, promoters utilized may regulate constitutive expression and include, but are not limited to, ADH1 and GPD. In a preferred embodiment, the first, second, third and fourth DNA constructs are each contained within a first, second, third and fourth expression vectors, the expression vectors comprising sequences that enable replication in both yeast and *E. coli*. DNA constructs isolated from insects, including, but not limited to, the dipteran species (for example, *D. melanogaster, A. aegypti*) and to *lepidopteran* species (for example, *C. fumiferana*) are contemplated to be within the scope of the present invention. Suitable reporter genes, which may be utilized include β-galactosidase, β-glucuronidase, green fluorescent protein, chloramphenicol acetyltransferase, and any surface molecules for which immunospecific antibodies are available.

In a particularly preferred embodiment, the altered ecdysone receptor has an alteration selected from the group consisting of a truncation, an insertion, a partial deletion of a the A/B domain, a full deletion of the A/B domain, site-directed and/or randomly mutagenized A/B domain. The receptor which heterodimerizes with the ecdysone receptor may also be altered, the alteration also being selected from the group consisting of a truncation, an insertion, a partial deletion of the A/B domain, a full deletion of the A/B domain, site-directed or randomly mutagenized A/B domain. Such altered receptors may have altered biological properties which facilitate the screening and identification of new and efficacious insecticidal compounds.

In yet another aspect of the invention, methods for utilizing the system described above are provided. An exemplary method for identifying insecticidal compounds which transactivate nuclear receptors in a ligand-dependent manner comprises the following: providing a host cell containing a first DNA construct having a nucleic acid molecule encoding an altered ecdysone receptor operably linked to a promoter; a second DNA construct having a nucleic acid molecule encoding a receptor which heterodimerizes with said altered ecdysone receptor upon transactivation, the nucleic acid molecule being operably linked to a promoter; a third DNA construct comprising a promoter containing a plurality of ecdysone response elements, the promoter being operably linked to a reporter gene and a fourth DNA construct encoding a co-activator molecule, said co-activator molecule being operably linked to a promoter sequence; contacting said host cell with an effective amount of a compound suspected to possess insecticidal activity; and assessing the level of ligand dependent co-activation mediated by the compound as indicated by expression levels of said reporter gene.

In a most preferred embodiment of the invention, a method for increasing expression of a gene of interest in a host in a ligand-dependent manner is provided. In gene expression applications, the reporter gene in the system can be replaced by any gene of interest, for example, a human gene encoding insulin. This method utilizes many of the components described above and comprises a first DNA construct having a nucleic acid molecule encoding an altered ecdysone receptor operably linked to a promoter; a second DNA construct having a nucleic acid molecule encoding a receptor which heterodimerizes with said altered ecdysone receptor upon transactivation, the nucleic acid molecule being operably linked to a promoter; a third DNA construct comprising a promoter containing a plurality of ecdysone response elements, the promoter being operably linked to a gene of interest; a fourth DNA construct encoding a co-activator molecule, the co-activator molecule also being operably linked to a promoter sequence; a host cell comprising said first, second, third and fourth DNA constructs; and contacting the host cell with an effective amount of a test agent or ligand suspected of transactivating expression of the gene of interest, increased expression of said gene of interest being dependent upon transactivation effectuated by an effective amount of said ligand. In a particularly preferred embodiment of the invention, expression levels of the gene of interest will reflect pharmacological doses of the transactivating ligand.

In one aspect, the system disclosed herein may be used for the detection of residues of pesticide chemicals that act as ecdysone receptor ligands. Genome sequencing approaches and Blast searches reveal that the ecdysone family of receptors are absent in most eukaryotic organisms. Thus the current vector system can be introduced into different organisms and used as a gene switching system for the controled up-regulation or down-regulation of the expression of a gene of interest. The system can also be applied to identify new proteins interacting with EcR, USP, RXR receptors and co-activators and functioning in ligand-dependent manner. Additionally, inasmuch as the components of the transactivating system described herein are conserved throughout evolution, the present system can be adapted for the screening and identification of transactivating ligands in other host cells besides yeast. Such systems include without limitation, the use of host cells derived from *C. elegans*, higher mammalian cells, and conventional tissue culture lines, e.g., those available from the ATCC. The system disclosed herein may also be utilized to advantage to assess structure/function relationships required for ecdysone mediated or ligand-mediated transactivation of target gene expression.

BRIEF DESCRIPTION OF THE DRAWINGS

In FIG. 4A, the DmUSP is inserted into the yeast expression vector to produce a ubiquitin (UBI)-fusion protein under the control of a CUP1 promoter. LEU2 is the leucine selectable marker and 2μ facilitates replication in yeast.

FIG. 5A shows the yeast expression plasmid for the full-length spruce budworm, CfEcR ecdysone receptor. The CfEcR coding sequence is inserted into the yeast expression vector to produce a ubiquitin (UBI)-fusion protein under the control of a CUP1 promoter. TRP1 is the tryptophan selectable marker and 2 μm facilitates replication in yeast.

In FIG. 6A the spruce budworm CfUSP coding sequence is inserted into the yeast expression vector to produce a ubiquitin (UBI)-fusion protein under the control of a CUP1 promoter. LEU2 is the leucine selectable marker and the 2 μm facilitates replication in yeast.

FIG. 7A shows the yeast expression plasmid for the full-length AaEcR. The *A. aegypti* EcR coding sequence is inserted into the yeast expression vector to produce a ubiquitin (UBI)-fusion protein under the control of a CUP1 promoter. TRP1 is the tryptophan selectable marker and 2μm facilitates replication in yeast.

FIG. 8A shows a yeast expression plasmid encoding the full-length *A. aegypti* USP a-form receptor. The mosquito *A. aegypti* USP a-form coding sequence is inserted into the yeast expression vector to produce a ubiquitin (UBI)-fusion protein under the control of a CUP1 promoter. LEU2 is the leucine selectable marker and 2.mu. facilitates replication in yeast.

FIG. 10B shows the impact of different ecdysteroidal analogs on transcription reduction in AaΔEcR/USPa/SMRT complex. The yeast strains carrying the reporter plasmid which contains 6 EcRE response elements coupled with *E. coli* β gal gene in combination with the presence of different plasmids for expression of different USPs, AaΔEcR and coactivators/repressors. The final concentration of all ecdysteroid analogues was 10 μM. The data are presented as a median set of at least 8 independent experiments plus SD.

DETAILED DESCRIPTION OF THE INVENTION

Figure 1:
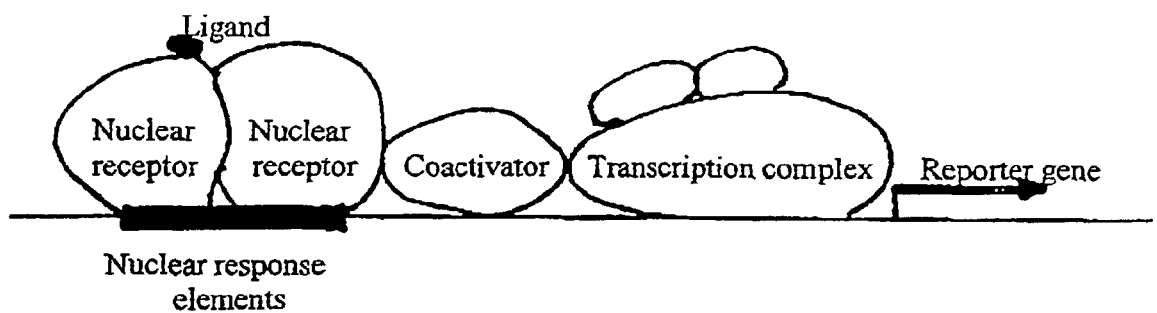
FIG. 1 is a schematic diagram of the ligand dependent transactivation system of the present invention.

In accordance with the present invention, compositions and methods are provided for identifying ligands of EcR and USP receptors. The functional expression of a mutated insect ecdysone receptor in yeast, e.g., *Saccharomyces cerevisiae,* is described herein. The reporter gene utilized in these studies contains the EcRE upstream of a CYC1 promoter which is coupled to the *E. coli* lacZ gene. The EcR receptor partner for heterodimerization—insect USP or mammalian retinoid X acid receptors (RXR), are also provided to assess ligand mediated transactivation of target gene expression.

In prior art co-expression studies, ecdysone receptor with its partner, insect USP or RXRs form the heterodimers EcR/USP or EcR/RXR respectively. These heterodimers are able to bind to ecdysone response elements (EcREs), and together with EcR ligands, activate transcription of a reporter gene in a constitutive, or, ligand independent fashion. Accordingly, the specific activation of ecdysone receptor pathway could not be assessed in this system.

In accordance with the present invention, it has been discovered that the ligand-dependent activation of reporter gene transcription requires the presence of a co-activator, such as GRIP1. Also required is the presence of at least one altered member of the heterodimeric receptor pair. EcR/USP/GRIP1 or EcR/RXR/GRIP1 complexes have been expressed in yeast cells containing an ecdysone responsive reporter plasmid. The expression system so created permits the development of a method for the rapid screening of ligands which effectively activate the EcR receptor. The method may also be utilized in screening for ligands for the USP receptor. Methods for modifying the EcR and USP receptor to achieve ligand-dependent transactivation are also described herein. In a particularly preferred embodiment, the altered ecdysone receptor has an alteration selected from the group consisting of a truncation, an insertion, a partial deletion of a the A/B domain, a full deletion of the A/B domain, site-directed and/or randomly mutagenized A/B domain. The receptor which heterodimerizes with the ecdysone receptor may also be altered, the alteration also being selected from the group consisting of a truncation, an insertion, a partial deletion of the A/B domain, a full deletion of the A/B domain, site-directed or randomly mutagenized A/B domain. Such altered receptors may have altered biological properties which facilitate the screening and identification of new and efficacious insecticidal compounds. The methods may be used to discover ligands for any orphan receptor which is capable of forming heterodimers with USPs or RXRs. Ligand-dependent expression of the reporter gene was shown to proceed in the presence of coactivators GRIP1 or co-repressors SMRT. Additionally, the methods of the invention may be used to advantage to identify new co-activators that can replace GRIP1 in the EcR/USP/GRIP1 or EcR/RXR/GRIP1 transactivation assays. The genetic alterations of the complex subunits described herein may be adapted to any subunit of a heterodimer, thus creating a new subunit that is highly responsive to a novel ligand.

The following definitions are provided to facilitate an understanding of the present invention.

As used herein, "reporter gene" refers to a gene whose expression may be assayed; such genes include, without limitation, β-galactosidase (LacZ), β-glucuronidase (GUS), alkaline phosphatase, amino acid biosynthetic genes, e.g., the yeast LEU2, HIS3, or LYS2 genes, nucleic acid biosynthetic genes, e. g. URA3 or ADE2 genes, the chloramphenicol acetyltransferase (CAT) gene, the green fluorescent protein (GFP) or any surface antigen gene for which specific antibodies are available. Additionally reporter genes may encompass any gene of interest whose expression may be detected.

In another version the reporter system comprises detection of an alteration in the structure of the receptor that occurs as a result of ligand binding. This alteration in structure may be detected by recruitment of ligand-bound receptor in a functional assay, e.g., the ligand bound receptor may become a substrate for degradation or alternatively association with another molecules which results in the generation of a fluorescent signal.

A "promoter" is a DNA sequence located proximal to the start of transcription at the 5' end of an operably linked transcribed sequence. The promoter may contain one or more regulatory elements or modules which interact in modulating transcription of the operably linked gene. An inducible promoter is a promoter which responds to the presence of different biochemical stimuli. Such promoters include, but are not limited to, the CUP1 promoter, heat shock promoters, galactose-inducible promoters and the like.

"Operably linked" describes two macromolecular elements arranged such that modulating the activity of the first element induces an effect on the second element. In this manner, modulation of the activity of a promoter element may be used to alter and/or regulate the expression of an operably-linked coding sequence. For example, the transcription of a coding sequence that is operably-linked to a promoter element is induced by factors that "activate" the promoter's activity; transcription of a coding sequence that is operably-linked to a promoter element is inhibited by factors that "repress" the promoter's activity. Thus, a promoter region is operably-linked to the coding sequence of a protein if transcription of such coding sequence activity is influenced by the activity of the promoter.

"Fusion construct" refers generally to recombinant genes which encode fusion proteins. The term "fusion protein gene" refers to a DNA sequence which encodes a fusion protein. A fusion protein gene may further provide transcriptional and translational regulatory elements for the transcriptional and translational control thereof.

A "fusion protein" is a hybrid protein, i.e., a protein which has been constructed to contain domains from at least two different proteins. As used herein, a fusion protein is a hybrid protein which possesses (a) transcriptional regulatory domain from a transcriptional regulatory protein, or (b) a DNA binding domain from a DNA binding protein linked to a heterologous protein to be assayed for interaction. The structure of the fusion protein is such that the transcriptional regulatory domain and the DNA binding domain are arranged in a manner that allows both domains to be biologically active. The protein that is the source of the transcriptional regulatory domain is different from the protein that is the source of the DNA binding domain. In other words, the two domains are heterologous to each other.

The transcriptional regulatory domain of the fusion protein may either activate or repress transcription of target genes, depending on the native biological activity of the domain.

"Expression" is the process by which the information encoded within a gene is revealed. If the gene encodes a protein, expression involves both transcription of the DNA into mRNA, the processing of mRNA (if necessary) into a mature mRNA product, and translation of the mature mRNA into protein. A nucleic acid molecule, such as a DNA or gene is said to be "capable of expressing" a polypeptide if the molecule contains the coding sequences for the polypeptide and the expression control sequences which, in the appropriate host environment, provide the ability to transcribe, process and translate the genetic information contained in the DNA into a protein product, and if such expression control sequences are operably-linked to the nucleotide sequence that encodes the polypeptide.

As used herein, a "cloning vector" is any entity that is capable of delivering a nucleic acid sequence into a host cell for cloning purposes. Examples of cloning vectors include plasmids or phage genomes. A plasmid that can replicate autonomously in the host cell is especially desired. Alternatively, a nucleic acid molecule that can insert (integrate) into the host cell's chromosomal DNA is useful, especially a molecule which inserts into the host cell's chromosomal DNA in a stable manner, that is, a manner which allows such molecule to be inherited by daughter cells.

Cloning vectors are often characterized by one or a small number of endonuclease recognition sites at which such DNA sequences may be cut in a determinable fashion without loss of an essential biological function of the vehicle, and into which DNA may be spliced in order to bring about its replication and cloning.

The cloning vector may further contain a marker suitable for use in the identification of cells transformed with the cloning vector. For example, "a marker gene" may be a gene which confers resistance to a specific antibiotic on a host cell.

As used herein, an "expression vector" is a vehicle or vector similar to the cloning vector but is especially designed to provide an environment which allows the expression of the cloned gene after transformation into the host. One manner of providing such an environment is to include transcriptional and translational regulatory sequences on such expression vectors, such transcriptional and translational regulatory sequences capable of being operably linked to the cloned gene. Another manner of providing such an environment is to provide a cloning site or sites on such vector, wherein a desired cloned gene and desired expression regulatory elements may be cloned. In an expression vector, the gene to be cloned is usually operably-linked to certain control sequences such as promoter sequences. Expression control sequences will vary depending on whether the vector is designed to express the operably-linked gene in a prokaryotic or eukaryotic host and may additionally contain transcriptional elements such as enhancer elements, termination sequences, tissue-specificity elements, and/or translational initiation and termination sites.

The phrase "consisting essentially of" when referring to a particular nucleotide or amino acid means a sequence having the properties of a given sequence. For example, when used in reference to an amino acid sequence, the phrase includes the sequence per se and molecular modifications that would not affect the basic and novel characteristics of the sequence.

A "host" refers to any organism or cell line that is the recipient of a cloning or expression vector. In preferred embodiments, the host of the invention is a yeast cell or a cultured animal cell such as a mammalian or insect cell. In an especially preferred embodiment, the yeast host is *Saccharomyces cerevisiae*.

A "binding moiety" is a stretch of amino acids which is capable of directing specific polypeptide binding to a particular DNA sequence (i.e., a "protein binding site"). Also referred to herein as a DNA binding domain, these proteins may be homodimers, heterodimers or monomers that bind DNA in a sequence specific manner.

"Purified DNA" is DNA that is not immediately contiguous with both of the coding sequences with which it is immediately contiguous (one of the 5' end and one of the 3' end) in the naturally occurring genome of the organism from which it is derived. The term therefore includes, for example, a recombinant DNA which is incorporated into a vector; into an autonomously replicating plasmid or virus; or into the genomic DNA of a prokaryote or eukaryote, or which exists as a separate molecule (e.g., a cDNA or a genomic DNA fragment produced by PCR or restriction endonuclease treatment) independent of other sequences. It also includes a recombinant DNA which is part of a hybrid gene encoding additional polypeptide sequence.

"Substantially identical", in reference to an amino acid sequence, means an amino acid sequence which differs only by conservative amino acid substitutions, for example, substitution of one amino acid for another of the same class (e.g., valine for glycine, arginine for lysine, etc.) or by one or more non-conservative substitutions, deletions, or insertions located at positions of the amino acid sequence which do not destroy the function of the protein (assayed, e.g., as described herein). A "substantially identical" nucleic acid sequence codes for a substantially identical amino acid sequence as defined above.

A "transformed cell" is a yeast or bacterial cell into which (or into an ancestor of which) exogenous DNA has been introduced by means of recombinant DNA techniques.

The phrase "positioned for expression" refers to a DNA coding molecule which is positioned adjacent to a DNA sequence which directs transcription and translation of the sequence.

A "purified antibody" is an antibody at least 60 weight percent of which is free from the proteins and naturally-occurring organic molecules with which it is naturally associated. Preferably, the preparation comprises antibody in an amount of at least 75 weight percent, more preferably at least 90 weight percent, and most preferably at least 99 weight percent. Such antibodies may be used to advantage for detecting expression of the reporter genes or for detection of ligand dependent expression a gene of interest.

"Ligands" are small compounds such as chemical molecules or small peptides that are able to bind to the target proteins (for example, the receptor heterodimers described herein). By interaction with target proteins ligands, change conformation of the protein and thereafter activate or inactivate the proteins. "Response elements" are specific DNA sequences located in promoters of hormone-inducible genes. Nuclear receptors in the form of homodimers, heterodimers or monomers bind specifically to these DNA regions to initiate or repress transcription of the targeted genes in the presence or the absence of ligands for the said nuclear receptors.

Preparation of Nucleic Acid Molecules Encoding the Proteins of the Invention and Uses Thereof in Assay Methods and Kits A. Nucleic Acid Molecules Nucleic acid molecules encoding the expression plasmids of the invention may be prepared by two general methods: (1) They may be synthesized from appropriate chemical starting materials, or (2) they may be isolated from biological sources. Both methods utilize protocols that are well known in the art.

The availability of nucleotide sequence information, for the Ecdysone receptor, the USP receptor, RXR receptors and GRIP1, enables preparation of the expression plasmids of the invention using conventional DNA cloning methods. The GenBank accession numbers for the various nucleic acid molecules described herein are as follows: AaEcR (p49880), DmEcR (M71078.1), CfEcR (AF092030.2), DmUSP (S11513), CfUSP (AF016368), human RXR α (X52773), mouse RXR β (X66224) or mouse RXR γ (X66225), GRIP1 (U39060.1). The mosquito *A. aegypti* USP a and b-form protein sequences are not available in the GenBank database, but have been published (10). Synthetic oligonucleotides may be prepared by the phosphoramadite method employed in the Applied Biosystems 38A DNA Synthesizer or similar devices. The resultant construct may be purified according to methods known in the art, such as high performance liquid chromatography (HPLC). Long, double-stranded polynucleotides, such as a DNA molecule encoding a construct of the present invention, must be synthesized in stages due to the size limitations inherent in current oligonucleotide synthetic methods. Thus, for example, a 3 kilobase double-stranded molecule may be synthesized as several smaller segments of appropriate complementarity. Complementary segments thus produced may be ligated such that each segment possesses appropriate cohesive termini for attachment of an adjacent segment. Adjacent segments may be ligated by annealing cohesive termini in the presence of DNA ligase to construct an entire 3 kilobase double-stranded molecule. A synthetic DNA molecule so constructed may then be cloned and amplified in an appropriate vector. Nucleic acid sequences encoding the components of the expression plasmids of the invention may be isolated from appropriate biological sources using methods known in the art. For example, RNA isolated from an insect may be used as a suitable starting material for the generation of cDNA molecules encoding the various different receptor proteins.

In accordance with the present invention, nucleic acids having the appropriate level of sequence homology with the protein coding region of the DNA molecules of the present invention may be identified by using hybridization and washing conditions of appropriate stringency. For example, hybridizations may be performed, using a hybridization solution comprising, for example, 5× SSC, 5× Denhardt's reagent, 1.0% SDS, 100 Mg/ml denatured, fragmented salmon sperm DNA, 0.05% sodium pyrophosphate and up to 50% formamide. Hybridization is carried out at 37–42° C. for at least six hours. Following hybridization, filters are washed as follows: (1) 5 minutes at room temperature in 2× SSC and 1% SDS; (2) 15 minutes at room temperature in 2× SSC and 0.1% SDS; (3) 30 minutes–1 hour at 37° C. in 1× SSC and 1% SDS; (4) 2 hours at 42–65° C. in 1× SSC and 1% SDS, changing the solution every 30 minutes.

One common formula for calculating the stringency conditions required to achieve hybridization between nucleic acid molecules of a specified sequence homology is as follows (Sambrook et al., 1989):

$$T_m = 81.5° C. + 16.6 \text{ Log}[Na+] + 0.41 (\% \ G+C) - 0.63 (\% \text{ formamide}) - 600/\#bp \text{ in duplex}$$

As an illustration of the above formula, using [Na+]=[0.368] and 50% formamide, with GC content of 42% and an average probe size of 200 bases, the $T_m$ is 57° C. The $T_m$ of a DNA duplex decreases by 1–1.5° C. with every 1% decrease in homology. Thus, targets with greater than about 75% sequence identity would be observed using a hybridization temperature of 42° C. Such a sequence would be considered substantially homologous to the sequences of the present invention.

Nucleic acids encoding the fusion proteins of the invention may be maintained as DNA in any convenient cloning vector. In one embodiment, clones are maintained in plasmid cloning/expression vectors, such as pRS plasmids series (17), or YEpE12 derivative plasmids (6). pBluescript plasmids (Stratagene, La Jolla, Calif.) or recombinant baculovirus transfer vector plasmids, such as pFastBac vectors (Gibco-BRL, Gaithersburg, Md.) that are propagated in insect and E. coli host cells, may also be employed.

The nucleic acids of the invention may also be used as starting materials for the generation of sequence variants or truncation mutants of the nucleic acids of the invention using any number of synthetic and molecular biologic procedures well known in the art including, but not limited to, truncation at available restriction sites and site-directed mutagenesis techniques. Particular mutations may give rise to receptor proteins with altered characteristics such as increased or decreased ligand binding activity.

B. Fusion Proteins

Many of the proteins in the invention are expressed in yeast as ubiquitin fusion proteins. Ubiquitin fusion enhances but is not necessary for protein expression in yeast. After translation of recombinant proteins, the 76 amino acids of ubiquitin sequence in the N-terminus is cleaved by the host ubiquitin pathway and native proteins are released. It is widely known that the presence of the ubiquitin sequence improves the expression of proteins of interest in yeast and E. coli (3).

The fusion proteins of the present invention may be prepared in a variety of ways, according to any number of known methods.

The availability of nucleic acid molecules encoding the components of the fusion proteins enables production of the fusion proteins using in vitro expression methods known in the art. For example, a cDNA or gene may be cloned into an appropriate in vitro transcription vector, such as pSP64 or pSP65 for in vitro RNA synthesis, followed by cell-free translation of the RNA in a suitable cell-free translation system, such as extracts of wheat germ, rabbit reticulocytes or HeLa cells. In vitro transcription and translation systems are commercially available (e.g., Promega Biotech, Madison, Wis.; Gibco-BRL, Gaithersburg, Md.).

C. Assay Methods and Kits

The expression plasmids of the invention may be used in a variety of ways having utility in research, insecticidal and pharmaceutical applications. Representative methods of use for the compositions of the invention are described below.

In a preferred embodiment, the expression plasmids of the invention may be used in the generation of cell lines or cellular systems that express the proteins described herein. Such cell lines exhibiting the ligand-dependent transactivation pathway of the invention may be used to advantage to identify new insecticidal reagents and other molecules that impact the steroid hormone receptor transactivation pathway. This expression system has utility in methods for assaying materials for antagonistic or agonistic activity toward the ecdysone and USP receptors. For example, assays may be established whereby intact cells expressing the proteins of the invention are contacted with agents or materials suspected of affecting the intracellular activity of the ecdysone or USP receptors, and the affect of such agents on ligand dependent transactivation activity is measured. The effect of such agents on the ligand dependent transactivation activity may be measured in any number of ways. For example, such cell systems may utilize a reporter system in which the production of the reporter signal is dependent on ligand dependent transactivation. Numerous reporters may serve equally well in this application including but not limited to, beta-galactosidase, alkaline phosphatase, fluorescent green protein and the like. Furthermore, the methods of the invention may be practiced in bacterial, fungal, insect, avian, mammalian or plant cells. However, yeast-based cell systems are preferred. Additional applications may be envisioned once the nature of the particular agent is clear.

The protein compositions of the invention have utility in assays for the detection and identification of agents capable of interacting with or affecting the proteins described herein. Assays may be established in which receptor polypeptide sequences of the invention are provided and then contacted with agents or materials suspected of interacting with such sequences. For example, upon provision of a receptor protein of the invention, or fragment or portion thereof, contacted agents may be assessed for their ability to bind specifically to the protein. Such binding agents would then have potential insecticidal utility. Such binding agents may further affect the functional activity of the receptor proteins, such as either inhibiting or enhancing transactivation function. Agents that inhibit the function of the ecdysone receptor or USP receptor protein would have potential utility in applications involving the prevention or treatment of insect infestation in crops for example.

Assays involving the cell based systems of the invention may be formatted in any number of configurations. Particularly useful for evaluating large numbers of agents and materials are high throughput screening formats. Traditionally such assays were typically formatted in 96 well plates. However, 384, 864 and 1536 well plates may be used in such high throughput assay systems. These systems are often automated using robotics technologies to allow manipulation and processing of large numbers of samples. The agents or materials that may be evaluated in the various assay methods of the invention for potential antagonistic or agonistic affects include but are not limited to small molecules, polymers, peptides, polypeptides, proteins, immunoglobulins or fragments thereof, oligonucleotides, antisense molecules, peptide-nucleic acid conjugates, ribozymes, polynucleotides and the like.

Another feature of the invention includes kits to facilitate the use of the compositions and methods disclosed herein. Exemplary kits would include the expression plasmids of the invention, and/or variants thereof. Also included would be protocols for use of the compositions of the invention for the particular application and the necessary reagents to carry out the application. Such reagents may include, but not be limited to, buffers, solvents, media and solutions, substrates and cofactors, vectors and host cells, and detection or reporter reagents. Accessory items may include vials, vessels, reaction chambers and instruction sheets.

The following protocols are provided to facilitate construction of the expression plasmids for use in the practice of the present invention.

A. Construction of A Reporter Plasmid Containing Ecdysone Response Elements

Plasmid pBRSS 6× EcRE-lac Z is reporter plasmid carrying 6 copies of ecdysone reponse element (5'AGAGA-CAAGGGTTCAATGCACTTGTCCAAT-3'; SEQ ID NO: 1) derived from the *D. melanogaster* hsp27 heat shock protein gene (15). See FIG. 2. These response elements are cloned upstream of the iso-1-cytochrome c (CYC1) promoter at position—250 nt at an Xho I site. The promoter was then operably linked to the *E. coli* beta-galactosidase gene (lac Z), such that expression of enzyme is regulated by the hybrid 6× EcRE-CYC1 promoter. (16).

B. Construction of A Vector for Expressing Glucocorticoid Receptor Interaction Protein, GRIP1 in Yeast The Nsi I-BamH I (GRIP1 gene with ADH1 promoter) fragment from pGRIP812 (8) was blunt-ended and cloned into the Pvu II site of the pRS423 (17). The GenBank accession number for GRIP1 is U39060.1. The resulting plasmid, pRS423-ADH1GRIP812 is a multicopy *E. coli*-yeast expression vector with yeast HIS3 selective marker. GRIP1 is constitutively expressed under the ADH1 promoter.

C. Expression of Mammalian Retinoid X Receptors (RXR)

The human RXR α (Genbank accession number X52773), mouse RXR β (Genbank accession number X66224) or mouse RXR γ (Genebank accession number X66225) subtypes were expressed in yeast-*E. coli* multicopy 2μ expression plasmids under regulation of CUP1 promoter with the LEU2 selective marker (1).

Figure 3A:
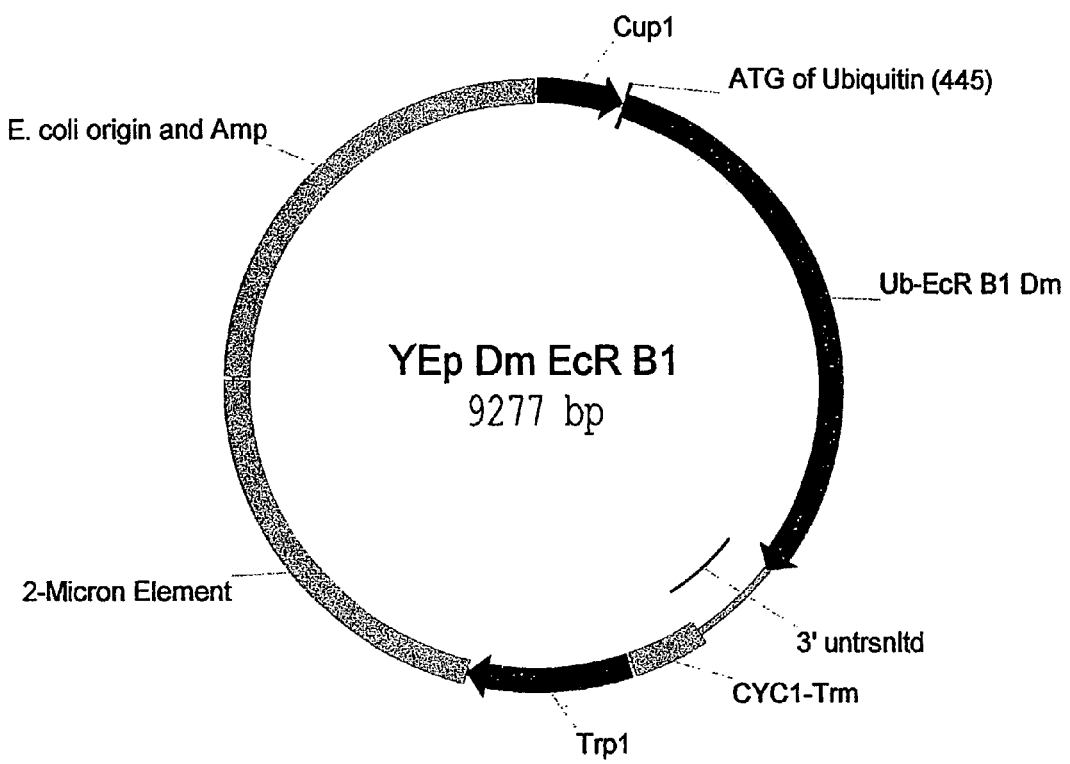
FIGS. 3A (YEpDmEcR) and 3B (YEpDm ΔN EcR) are schematic diagrams of the yeast expression plasmids utilized in the practice of the present invention. YEpDmEcR is a yeast expression plasmid encoding the full-length *D. melanogaster* EcR B-1 ecdysone receptor (FIG. 3A). The *D. melanogaster* EcR B-1 coding sequence is inserted into the yeast expression vector to produce a ubiquitin (UBI)-fusion protein under the control of a CUP1 promoter. TRP1 is the tryptophan selectable marker and 2μ is for replicating yeast DNA.

D. Construction of A Vector for Expressing Full-Length *D. melanogaster* Ecdysone Receptor (Dm EcR) in Yeast The *Drosophila melanogaster* EcR B-1 cDNA (11), GeneBank accession number is M71078.1, was used as a source for plasmid construction. The 5'- N-terminal of the coding sequence of the *D. melanogaster* ecdysone receptor EcR B-1 cDNA was amplified using two primers AflII-UbEcR-5' (5'-CTTGTCTTAAGACTAAGAGGTGGT atgaagcggcgctggtcgaac-3'; SEQ ID NO: 2) and Nco I-EcR-3' (5'-tgctgacttaggccatggccgt-3'; SEQ ID NO: 3). (See FIG. 3A). The upper case letters indicate sequence corresponding to ubiquitin, lower case letters indicate sequences corresponding to Dm EcR B-1. The AflII and Nco I sites are underlined. This fragment spans the coding sequence for 70 amino acids of Dm EcR. The PCR fragment was digested with Afl II-NcoI and recloned into the Afl II-NcoI site of the plasmid YEpUbOCT1. Plasmid YEpUbOCT1 is a yeast-*E. coli* 2 micron multicopy expression vector with TRP1 as the yeast selective marker, containing human ubiquitin (UBI) under yeast CUP1 promoter and CYC1 transcription terminator after ubiquitin sequence). Accordingly, the EcR is fused in frame 5'-prime of ubiquitin. Next, the NcoI-Afl II fragment (Afl II is blunt-ended by Klenow DNA polymerase) of EcR B-1 from cDNA EcR was cloned into the NcoI- Acc 65 I of the intermediate plasmid obtained above (Acc65 I is blunt-ended by Klenow DNA polymerase). The resulting plasmid, YEp DmEcR contains the full-length EcR B-1 fused with ubiquitin sequence. Expression is driven by the CUP1 promoter and selection of transformants is achieved using the TRP1 selective marker.

E. Construction of a Yeast Expression Vector Encoding the *D. melanogaster* Ecdysone Receptor Containing a Deletion of the AF-1 Domain (Dm ΔN ECR)

The plasmid YEp Dm ΔN EcR is essentially similar to plasmid YEp Dm EcR described above. However in this plasmid the A/B (AF-1) domain of the Dm EcR is partially deleted (up to the EcoR I site of Dm EcR, i.e. the first 220 amino acids up to VNSSISS sequence (SEQ ID NO: 25) have been removed). The resulting sequence is inserted into the yeast expression vector to produce a ubiquitin (UBI) ΔN EcR fusion protein under the control of a CUP1 promoter. TRP1 is the tryptophan selectable marker and 2μ facilitates replication in yeast.

F. Construction of Yeast Expression Vector for Full-Length *D. melanogaster* Ultraspiracle Receptor (DmUSP)

The DmUSP cDNA clone was used as a source for plasmid construct. GeneBank accession number for DmUSP is S11513. The N-terminal coding sequence of the Dm USP receptor (7) was amplified using two primers: (Afl II primer: 5'-TTGTCTTAAGACTAAGAGGTGGT atggacaactgcgac-cagg-3' (SEQ ID NO: 4) and Nco I: 5'-agcaggtggaccatga-catgg-3' (SEQ ID NO: 5). The upper case letters indicate the sequence which corresponds to ubiquitin. The lower case letters indicating sequences corresponding to DmUSP receptor. The Afl II and Nco I sites are underlined. The amplified fragment contains DNA sequence encoding the first 50 amino acids of the USP receptor. The PCR fragment was digested with Afl II-NcoI and cloned into the Afl I-NcoI of the plasmid YEpUbOCT1 similar to that described for cloning the plasmid YEp Dm EcR. The resulting plasmid contains the USP receptor sequence fused 5' in frame with ubiquitin. Next, the NcoI- Afl II fragment of the USP receptor cDNA (7) was cloned into the NcoI- Acc 65 I of the intermediate plasmid obtained above. (Both Afl II and Acc 65 I are blunt-ended by Klenow DNA polymerase). The resulting plasmid, YEp DmUSP encodes the full-length of USP receptor sequence fused in frame with ubiquitin sequences, expression of each being drive by the CUP1 promoter. The TRP1 selective marker is included to facilitate selection of transformants. See FIG. 4A.

The USP receptor sequence was also shuffled to another plasmid pRS425 ER alpha, containing the LEU2 marker (pRS425 ER alpha - plasmid pRS425 (17) with human estrogen receptor ER alpha fused to ubiquitin under CUP1 promoter via the following the protocol. The SalI-MluI fragment containing a portion of ubiquitin and the entire coding region of the USP receptor sequence from YEp Dm USP was cloned into the SalI-MluI site of pRS425 ER alpha. The resultant plasmid, pRS425-DmUSP, contains a multicopy LEU2 selective marker. The USP sequence is fused in frame with ubiquitin (UBI) and expression is driven by the CUP1 promoter.

F. Construction of a Yeast Expression Vector Encoding the *D. melanogaster* Ultraspiracle Receptor (Dm USP) Containing a Deletion of the AB Transactivation Domain (Dm ΔAB USP)

The yeast expression vector encoding the DmUSP with an AB domain deletion was constructed as follows. The pRS425-Dm USP plasmid containing the full coding sequence of the DmUSP was used to amplify an N-terminally truncated DmUSP. First, the AB domain deleted DmUSP was amplified using two primers: Dm ΔAB USP-5':5'-AGGAGTCGACCTTACATCTTGTCTTAA-GACTAAGAGGTGGTatgtatccgcctaaccatcc gctgagc-3'; SEQ ID NO: 6. (Upper case letters indicate the nucleotide ubiquitin sequence; lower case letters denote the nucleotide sequence of 5'-terminus of DmUSP starting from YPPNH (SEQ ID NO: 26).) The Sal I site is underlined. The second primer, DmUSP-3':5'-AAGGACGCGTcttttcggttagagcg-gatg-3' (SEQ ID NO: 7) shows the Mlu I site which is underlined. The lower case letters indicate the nucleotide sequence of the 3' terminus of Dm USP cDNA. The DNA fragments were amplified in 30 cycles (96° C.- 30 seconds, 54° C.- 1 minute and 72° C.- 3 minutes) using high replication fidelity Deep Vent Polymerase (New England Biolabs). The PCR products were purified and digested with Sal I and Mlu I and subsequently recloned into Sal I-Mlu I sites of the yeast expression vector with LEU2 marker, pRS425-ER alpha, described above.

F. Construction of A Yeast Expression Vector Encoding the Full-Length Spruce Budworm *C. fumiferana* Ecdysone Receptor (CfEcR)

Figure 5A:
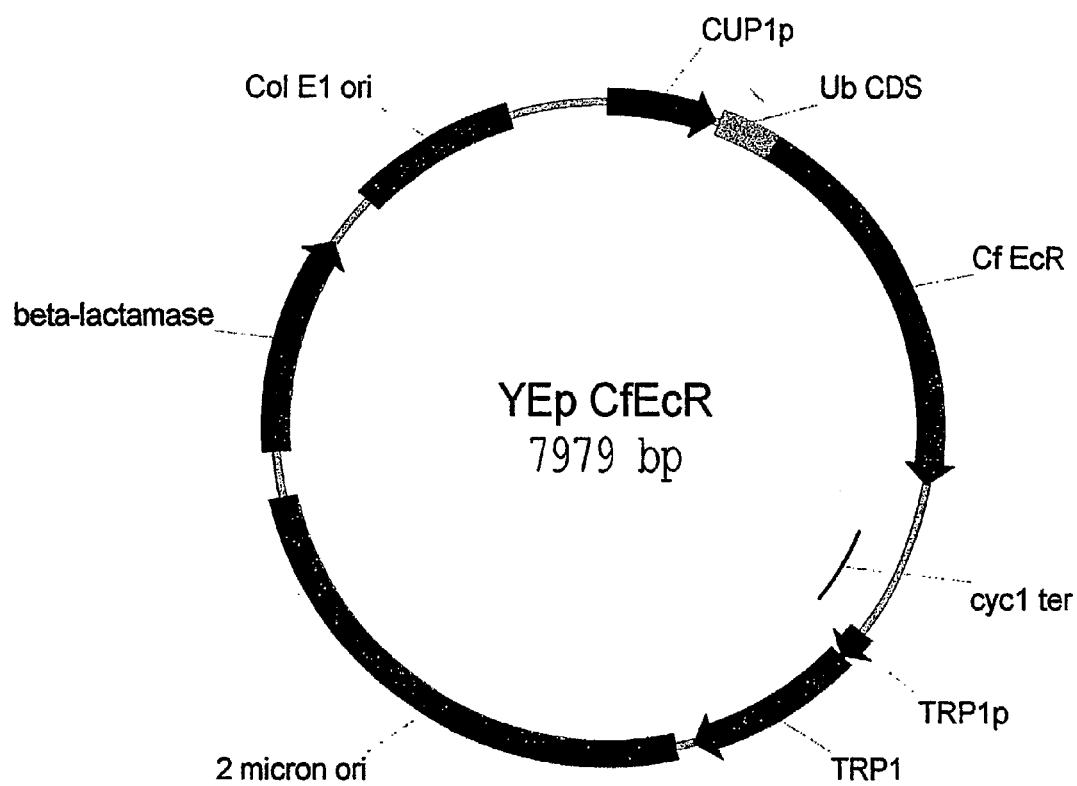
FIGS. 5A (YEpCfEcR) and 5B (YEpCfΔAB EcR) show plasmids expressing full-length *C.fumiferana* (Cf) CfEcR and a CfEcR containing an AB domain deletion.

The full-length coding sequence of the CfEcR (GeneBank accession number AF092030.2) was fused in frame at the N-terminus with human ubiquitin, expression of the fusion protein being driven by the CUP1 promoter (plasmids YEpCfEcR). See FIG. 5A. The multicopy yeast expression plasmid YEp CfEcR was constructed based on plasmid YEpE12 (6). YEpE12 contains TRP1 as a yeast selective marker, and ubiquitin sequences fused with the human estrogen receptor sequence under the CUP1 promoter. The following primer pairs, Cf EcR-SalI and Cf EcR-Sac1 were used for amplification of full-length CfEcR-A from the cDNA reported in (12). The Cf EcR-Sal 1 primer has the following sequence: 5'-AGGAGTCGACCTTACATCT-TGTCTTAAGACTAAGAGGTGGTatggacct gaaacac-gaagtggcttaccg-3' SEQ ID NO: 8. The upper case letters indicate the nucleotide sequence corresponding to human ubiquitin. The Sal I site suitable for insertion of the ubiquitin sequence is underlined. Lower case letters denote the sequences corresponding to the Cf EcR starting from ATG. The Cf EcR-SacI primer has the following sequence: 5'-AAGGGAGCTC taatctcccgcgcattc-3'; SEQ ID NO: 9. The lower case letters indicate the nucleotide sequences corresponding to the 3' terminus of the Cf EcR sequence and the SacI restriction site is underlined. The DNA fragments were amplified in 30 cycles (96° C.-30 seconds, 54° C.-1 minute and 72° C.-3 minutes) using high replication fidelity Deep Vent Polymerase (New England Biolabs). The PCR products obtained following amplification were digested with Sal I and Sac I and subsequently recloned into the Sal I and Sac I sites of the plasmid YEpE12 (6).

I. Construction of Yeast Expression Vector Encoding the Spruce Budworm, *C. fumiferana* (Cf) Ecdysone Receptor Containing a Deletion in the AB Transactivation Domain (Cf ΔAB EcR)

Figure 5B:
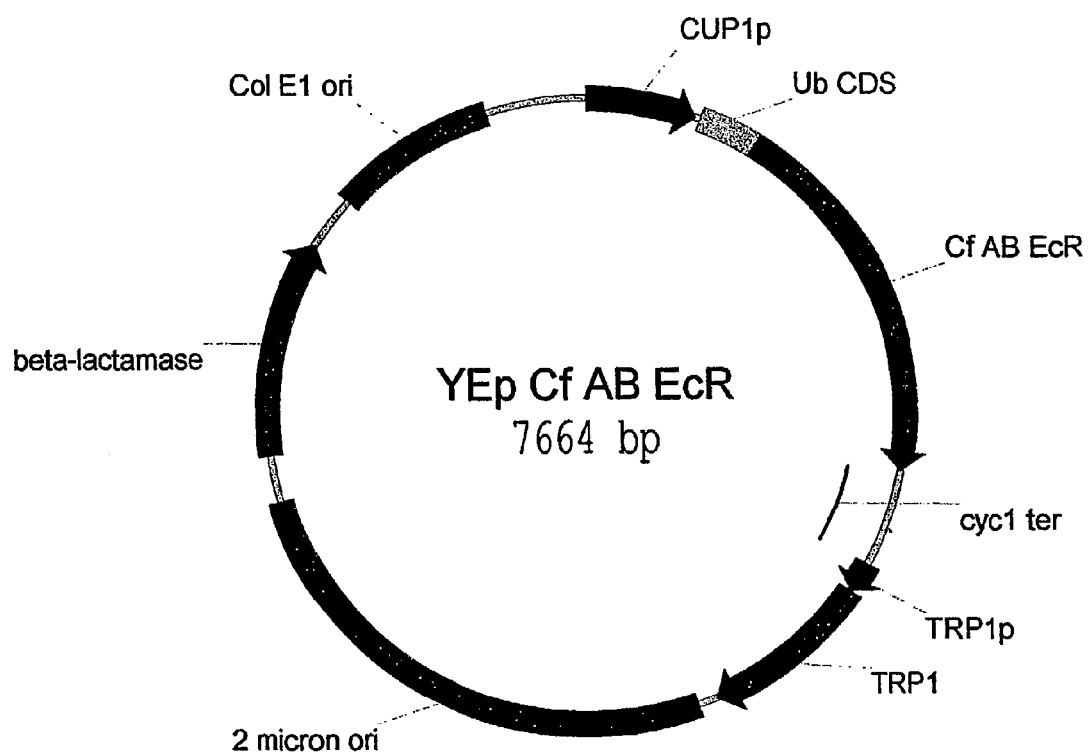
FIG. 5B shows the yeast expression plasmid for expressing CfEcR wherein the N-terminal A/B domain, i.e., the first 106 amino acids up to RQQEEL (SEQ ID NO: 27), have been deleted. The resulting construct is inserted into the yeast expression vector to produce a ubiquitin (UBI)-fusion protein under the control of a CUP1 promoter. LEU2 is the leucine (LEU2) selectable marker and 2μ facilitates replication in yeast.

Cf EcR sequences containing a deletion of the AB domain were fused in frame at the N-terminus with human ubiquitin. See FIG. 5B. Expression of the fusion protein is driven by the CUP1 promoter (YEp Cf ΔAB EcR). The multicopy yeast expression plasmid YEp Cf ΔAB EcR was constructed utilizing plasmid YEpE12 as a starting plasmid (6). YEpE12 contains TRP1 as a yeast selective marker, and ubiquitin sequences fused to human estrogen receptor sequences under control of the CUP1 promoter. The CfEcR with the A/B transactivation domain deletion was amplified from the cDNA clone (12) using the following primer pairs: Cf AB EcR-Sal I and Cf EcR-SacI. CfAB EcR -Sal I sequence is: 5'-AGGAGTCGACCTTACATCTTGTCTTAA-GACTAAGAGGTGGtatgcggcagcag gaggaactgtgtctg-3'; SEQ ID NO: 10. Upper case letters indicate the nucleotide sequence corresponding to human ubiquitin. The Sal I site suitable for insertion of the ubiquitin sequence is underlined. The lower case letters denote the sequence corresponding to the DNA binding domain of the Cf EcR starting from amino acids RQQEELCLV (SEQ ID NO: 28). In the Cf EcR-SacI primer (5'-AAGGGAGCTCtaatctccc gcgcattc-3'; SEQ ID NO: 11), the lower case letters indicate the nucleotide sequences corresponding to the 3' terminus of the Cf EcR. The SacI restriction site is underlined. The sequence of the EcR containing the AB domain deletion (ΔAB EcR) started at the beginning of the DNA binding domain with amino acid sequence RQQEELCLV (SEQ ID NO: 28). Following protein translation and ubiquitin cleavage, the N-terminal arginine "R" of the protein is exposed. Such terminal R residuces are potential signals for short lived proteins (2). To stabilize the protein, an additional methionine was added to the RQQEELCVL sequence (SEQ ID NO: 29) at the N+terminus. The DNA fragments were amplified in 30 cycles (96° C.-30 seconds, 54° C.-1 minute and 72° C.-3 minutes) using high replication fidelity Deep Vent Polymerase (New England Biolabs). The PCR products for Cf ΔAB EcR were digested with Sal I and Sac I and subsequently recloned into the Sal I and Sac I sites of plasmid YEpE12 (6).

J. Construction of A Yeast Expression Vector Encoding the Full-Length Spruce Budworm, *C. fumiferana* Ultraspiracle Receptor (CfUSP)

The yeast expression vector for Cf USP (GenBank accession number for CfUSP is AF016368) was synthesized as follows. Initially, the full-length Cf USP was amplified from a cDNA clone containing full-length coding sequence of CfUSP (13) using two primers: 1) Cf USP-5': 5'-AG-GAGTCGACCTTACATCTTGTCTTAAGAC-TAAGAGGTG Gtatgtcaagtgtggcgaag-3'; SEQ ID NO: 12;

Upper case letters correspond to the nucleotide sequence of ubiquitin. The lower case letters denote the nucleotide sequence corresponding to the 5'-terminus of the CfUSP starting from the ATG. The Sal I site is underlined; and 2) Cf USP-3'–5'-CCTTCCATGGgaatgtcaataatgcccgtg-3'; (SEQ ID NO: 13). The Nco I site is underlined. The lower case letters indicate the nucleotide sequence of the 3' terminus of CfUSP cDNA. The DNA fragments were amplified in 30 cycles (96° C.-30 seconds, 54° C.-1 minute and 72° C.-3 minutes) using high replication fidelity Deep Vent Polymerase (New England Biolabs). The PCR products were purified and digested with Sal I and Nco I and subsequently recloned in the Sal I-Nco I sites of a yeast expression vector containing a LEU2 selective marker, pRS425-ER alpha. This plasmid (pRS425-ER alpha) contains the BamH I-Pml I CUP1p-ER-cyc$_{ter}$ fragment from the YEpE12 plasmid. This fragment (6) was blunt-ended and then ligated into the Pvu II site of pRS425 (17). See FIG. 6A.

K. Construction of a Yeast Expression Vector Encoding the Spruce Budworm, C. fumiferana Ultraspiracle Receptor Containing a Deletion in the A/B Transactivation Domain (Cf ΔAB USP)

The yeast expression vector encoding the CfUSP deleted in the A/B transactivation domain was synthesized as follows: The CfUSP containing the A/B deletion was amplified from a cDNA clone containing full-length open reading sequence for CfUSP (13) using the following two primers: CfAB USP-5'5'-AGGAGTCGACCTTACATCTTGTCT-TAAGACTAAGAGGTGGT atgtacccgcctaatcacccctgagt-3'; (SEQ ID NO: 14) The upper case letters indicate the nucleotides corresponding to ubiquitin sequence. The lower case letters denote the 5'-terminal sequence of the CfUSP starting from YPPNH (SEQ ID NO: 26). The Sal I site is underlined) CfUSP-3': 5'-CCTTCCATGGgaatgtcaataatgc-ccgtg-3'; (SEQ ID NO: 15). The Nco I site is underlined. The lower case letters indicate the 3' terminal sequence of CfUSP cDNA. The DNA fragments were amplified in 30 cycles (96° C.-30 seconds, 54° C.-1 minute and 72° C.-3 minutes using high replication fidelity Deep Vent Polymerase (New England Biolabs). The PCR products were purified and digested with Sal I and Nco I and subsequently recloned in the Sal I-Nco I sites of the yeast expression vector containing a LEU2 marker, pRS425-ER.

L. Construction of a Yeast Expression Vector Encoding the Full-length Mosquito A. aegypti Ecdysone Receptor (AaEcR).

The yeast expression vector encoding the full length of AaEcR (plasmid YEpE12-AaEcR) was constructed similarly as described in the Section H above. The GenBank accession number for AaEcR is p49880. The following primer pairs, AaEcR-Sal I and AaEcR-Mlu I, were utilized were used for amplifying full-length of Aa EcR from mosquito A. aegypti cDNA clone (5). 1) Primer from 5' end of AaEcR—AaEcR-Sal1: 5'-AGGAGTCGACCTTAC ATCT-TGTCTTAAGACTAAGAGGTGGTatgat-gaaaagaagatggtcc-3' (SEQ ID NO: 16); the upper case letters indicating the nucleotide sequence belonging to human ubiquitin. The Sal I site present in the ubiquitin sequence is underlined. The lower case letters denote sequence corresponding to the AaEcR starting from ATG. 2) Primer from 3' end of AaEcR-AaEcR-Mlu I 5'-AAGGACGCGTtgaaca-gaatgtcgtccgct-3'; (SEQ ID NO: 17), the lower case letters correspond to sequences present at the 3' terminus of the AaEcR. The Mlu I restriction site is underlined. The DNA fragments were amplified in 30 cycles (96° C.-30 seconds, 54° C.-1 minute and 72° C.-3 minutes) using high replication fidelity Deep Vent Polymerase (New England Biolabs). The PCR products for full length Aa EcR were digested with Sal I and Mlu I and subsequently recloned into the Sal I and Mlu I sites of the plasmid YEpE12 (6).

M. Construction of a Yeast Expression Vector Encoding the Mosquito A. aegypti Ecdysone Receptor Containing a Deletion in the A/B Transactivation Domain (Aa ΔAB EcR).

Figure 7A:
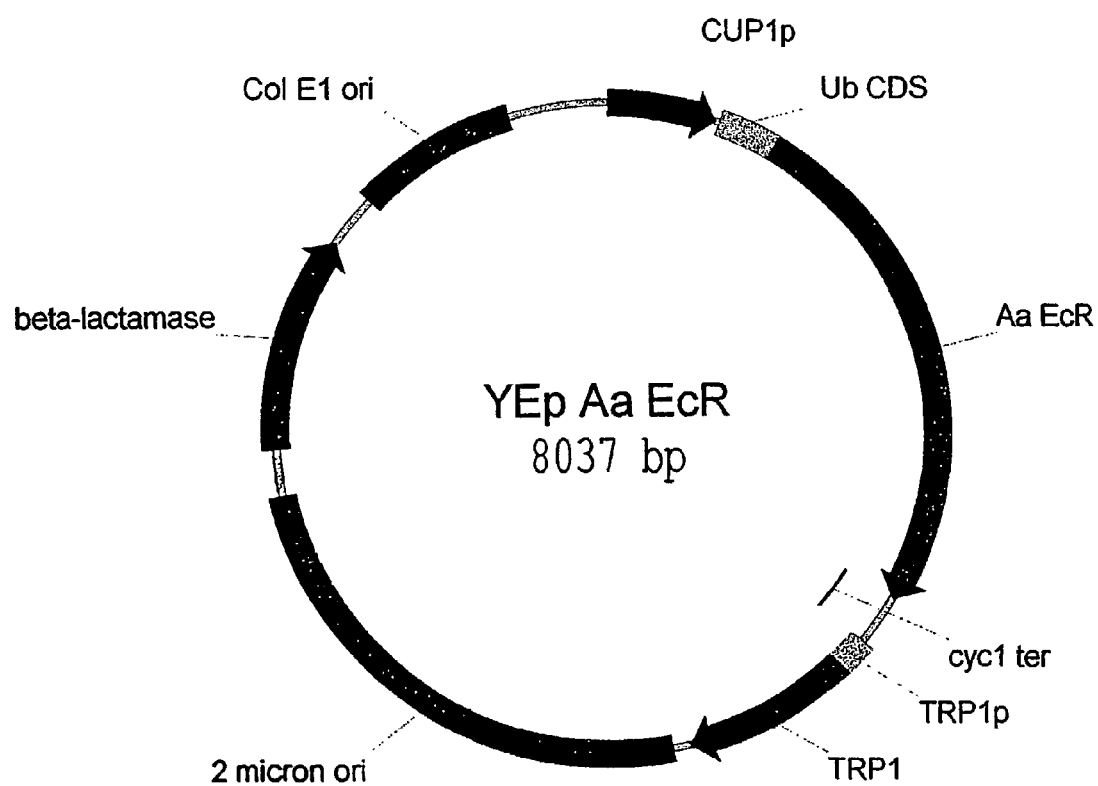
FIGS. 7A (YEpAaEcR) and 7B (YEpAaΔAB EcR) show plasmids expressing full-length mosquito *A. aegypti* (AaEcR) and an AaEcR containing an AB domain deletion (AazΔAB EcR).
Figure 7B:
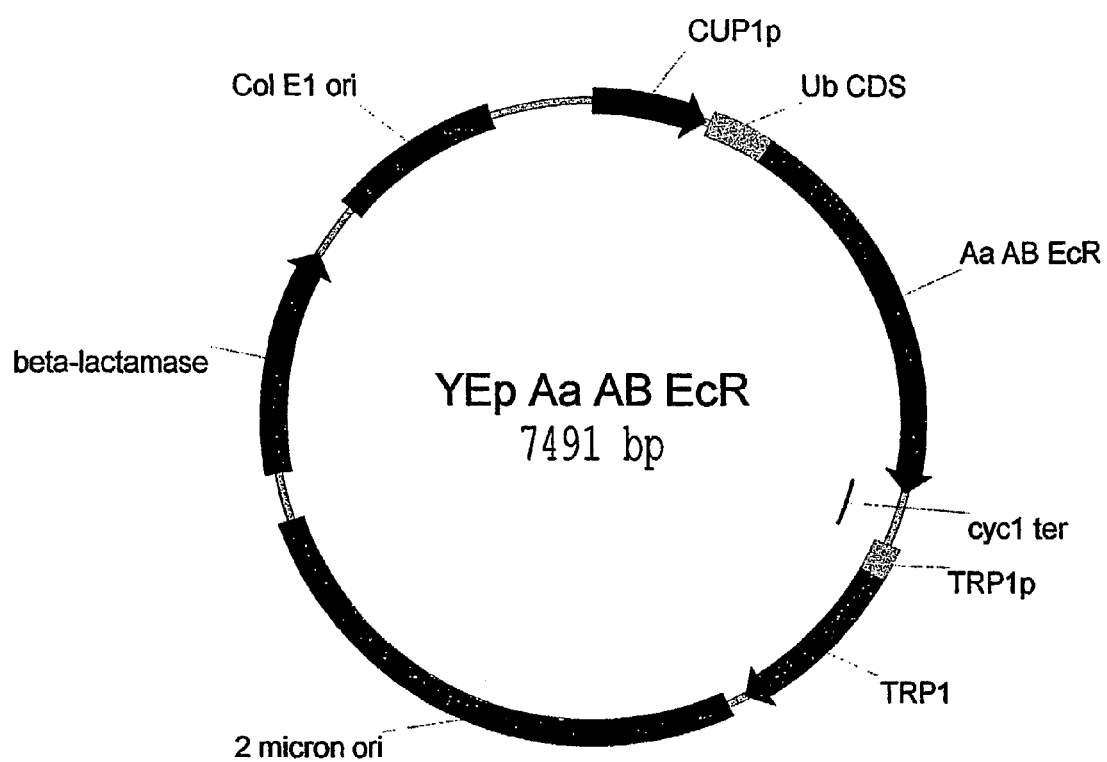
FIG. 7B shows the yeast expression plasmid for expressing Aa EcR wherein the N-terminal A/B domain, i.e., the first 183 amino acids up to RQQEEL (SEQ ID NO: 27), have been deleted. The resulting construct is inserted into the yeast expression vector to produce a ubiquitin (UBI)-fusion protein under the control of a CUP1 promoter. LEU2 is the Leucine (LEU2) selectable marker and 2 μm facilitates replication in yeast.

The yeast expression vector encoding the AaEcR containing a deletion in the A/B domain (plasmid YEpAa ΔAB EcR) was also synthesized from mosquito A. aegypti cDNA clone (5). See FIG. 7B. AaEcR receptor was amplified using the following primer pairs: AaEcR A/B-5'-Sal I and AaEcR-3'-MluI, AaEcR A/B-5'-Sal I has the following sequence 5'-AGGAGTCGACCTTA CATCTTGTCTTAAGACTAA-GAGGTGGTatgcggcagcaggaggaactgtgtctg-3':SEQ ID NO: 18) . The upper case letters correspond to the nucleotide sequence present in human ubiquitin. The Sal I site in the ubiquitin sequence is underlined. The lower case letters denote sequence corresponding to the DNA binding domain of the Aa EcR starting from amino acid RQQEELCLV (SEQ ID NO: 28). In AaEcR-3'-MluI: 5'-AAGGACGCGTtgaaca-gaatgtcgtccgct-3'; SEQ ID NO: 19; the lower case letters indicate the nucleotide sequences corresponding to the 3' terminus of the Aa EcR. The Mlu I restriction site is underlined. The deletion of the A/B domain encoding sequence (Aa ΔAB EcR) started from the beginning of the DNA binding domain at amino acid sequence RQQEELCLV (SEQ ID NO: 28). Following protein translation and ubiquitin cleavage, the exposed N-terminal "R" in the protein is a proposed signal for a short lived protein (2). To stabilize the protein, an additional methionine is added before the RQQEELCVL sequence (SEQ ID NO: 29). The DNA fragments were amplified in 30 cycles (96° C.-30 seconds, 54° C. 1 minute and 72° C.-3 minutes) using high replication fidelity Deep Vent Polymerase (New England Biolabs). The PCR products for Aa_AB EcR were digested with Sal I and Mlu I and subsequently recloned into the Sal I and Mlu I sites of the plasmid YEpE12, described above (6).

N. Construction of a Yeast Expression Vector Encoding the Full-length Mosquito A. aegypti Ultraspiracle Receptor AaUSP a- and b-form Mosquito A. aegypti expresses two forms of the ultraspiracle receptor, an a- and b-form, that differ in the N-terminal region of the A/B domain. See FIGS. 8A and 8B. The yeast expression vectors for a- and b-form (pRS425-AaUSPa and pRS425-AaUSPb) were constructed in a fashion similar to that described section J above. The a-form and b-form USP receptors were amplified from corresponding cDNAs clones (10) using the following primer pairs: (Aa USPa-5' and Aa USP-3') and (Aa USPb-5' and Aa USP-3'), respectively: Aa USPa-5': 5'-AGGAGTCGACCTTACATCTTGTCTTAA-GACTAAGAGGTGGT atgctgaagaaggaaaaacc-3' (SEQ ID NO: 20); and AaUSPb-5' 5'-AGGAGTCGACCTTACATCT-TGTCTTAAGACTAAGAGGTGGTatggatccc agcgatc-gagg-3' (SEQ ID NO: 21). The upper case letters correspond to ubiquitin sequence. The lower case letters correspond to the 5'-terminal sequence of the Aa USP a- and b-form respectively, starting from the ATG codon. The Sal I site is underlined. In Aa USP-3' 5'-AAGGACGCGTccacaagttgct-tgttctagg-3' (SEQ ID NO: 22), the Mlu I site is underlined. The lower case letters correspond to the 3' terminal sequence of Aa USP cDNA. The DNA fragments were amplified in 30 cycles (96° C.-30 seconds, 54° C.-1 minute and 72° C.-3 minutes) using high replication fidelity Deep Vent Polymerase (New England Biolabs). The PCR products for both a- and b-forms of USP were purified and digested with Sal I and Mlu I and subsequently recloned in the Sal I-Mlu I sites of the yeast expression vector with the LEU2 marker, pRS425-ER alpha.

O. Construction of a Yeast Expression Vector Encoding the Mosquito *A. aegypti* Ultraspiracle Receptor Containing a Deletion in the A/B Transactivation Domain (Aa ΔAB USP)

The yeast expression vector encoding the truncated AaUSP receptor was synthesized as follows. Initially, the AaUSP receptor sequence containing a deletion of the AB transactivation domain was amplified from cDNA clones of AaUSP (10)) using two primers : Aa ΔAB USP-5' and AaUSP-3': AaAAB USP-5': 5'-AGGAGTCGACCTTA-CATC TTGTCTTAAGACTAAGAGGTGGTatgtatccgcc aaatcatccgctcagc-3' (SEQ ID NO: 23). The upper case letters correspond to ubiquitin sequence. The lower case letters denote the 5'-terminal sequence of the AaUSP receptor starting from amino acid YPPNH. The Sal I site is underlined. In AaUSP-3': 5'-AAGGACGCGTcacaagttgcttgt-tctagg-3' (SEQ ID NO: 24), the MluI site is underlined. The lower case letters correspond to the 3' terminal of Aa USP receptor. The DNA fragments were amplified in 30 cycles (96° C.-30 seconds, 54° C.-1 minute and 72° C.-3 minutes) using high replication fidelity Deep Vent Polymerase (New England Biolabs). The PCR products were purified and digested with Sal I and Mlu I and subsequently recloned in the Sal I-Mlu I sites of the yeast expression vector with a LEU2 marker, pRS425-ER alpha.

P. Yeast Transformation

Briefly, yeast cells are cultured in 5 mL of YPD liquid medium overnight at 30° C. The cell culture was diluted 1:20 in YPD media and further grown until cell density reached an O.D of 0.6. at $OD_{600}$. The cells were pelleted by centrifugation and washed with 10 mL of TE+0.1M lithium acetate. Cells are then resuspended in 10 mL TE+0.1M lithium acetate and incubated at 30° C. for 1 hour. Cells are collected and resuspended in 0.5 mL of TE+ 0.1M lithium acetate. Aliquots of cells (50 µL), were incubated for 15 minutes at 30° C. with 1–2 µg plasmid DNA in the presence of 5 µg of denatured salmon sperm DNA as DNA carrier. In the case of co-transformation, the indicated plasmids were added simultaneously. 50% polyethyleneglycol of molecular weight 4000, diluted in TE, was added to a final concentration of 35%. DMSO was added to the transformation solution simultaneously to a final concentration 3%. The samples were mixed well by vortexing and incubated for an additional 30 minutes at 30° C. The cell mixture is then heated for 15 minutes at 42° C. Cells were then collected and plated onto appropriate yeast selective media. Transformants of 4 plasmids are selected on the complete media without tryptophan, uracil, leucine and histidine.

Q. β-Galactosidase Activity Assay

The yeast cells grown overnight in selective liquid media at 30° C. were diluted in prewarmed liquid selective media to 0.1 at $OD_{600}$ ($OD_{culture}$). 100 µl of the cell culture was spiked to each well of a.96-well microtiter plate. Ligand (2 µl diluted in DMSO) was added to each well giving a final concentration of DMSO of 2%. As a control, 2 µl of DMSO were also added to additional test wells. The final concentration of the tested compounds in the media is 10 µM. The cells were incubated in the presence of ligand in a shaker at 30° C. After 4 hours of incubation, 100 µl of 2× "Z" Sarcosine-ONPG buffer (120 mM $Na_2HPO_4$, 80 mM $NaH_2PO_4$, 20 mM KCl, 2 mM $MgSO_4$, 100 mM beta-mercaptoethanol (Sigma), pH 7.0, 0.4% lauroyl sarcosine (Sigma), 4 mg/mL ONPG (Diagnostic Chemicals limited) was added to each well and the plate was further incubated at 37° C. The 2× "Z" Sarcosine-ONPG buffer is freshly prepared or stored at −20° C. prior to use. After incubation at 37° C. for 1 hour. The reaction was stopped by adding 100 µL of quenching solution 0.5 M $Na_2CO_3$ and $OD_{405}$ ($OD_{reaction}$) and beta-galactosidase activity was measured in a micro plate reader (Biotek) at a wave length of 405–450 nanometers. The effect of copper on enhancement of the transactivation response mediated by the ligands tested was studied by adding $CuSO_4$ to the media to a final concentration of 10 µM.

The following examples are provided to describe the invention in further detail. These examples, which set forth the preferred mode presently contemplated for carrying out the invention, are intended to illustrate and not to limit the invention.

EXAMPLE I

Figure 2:
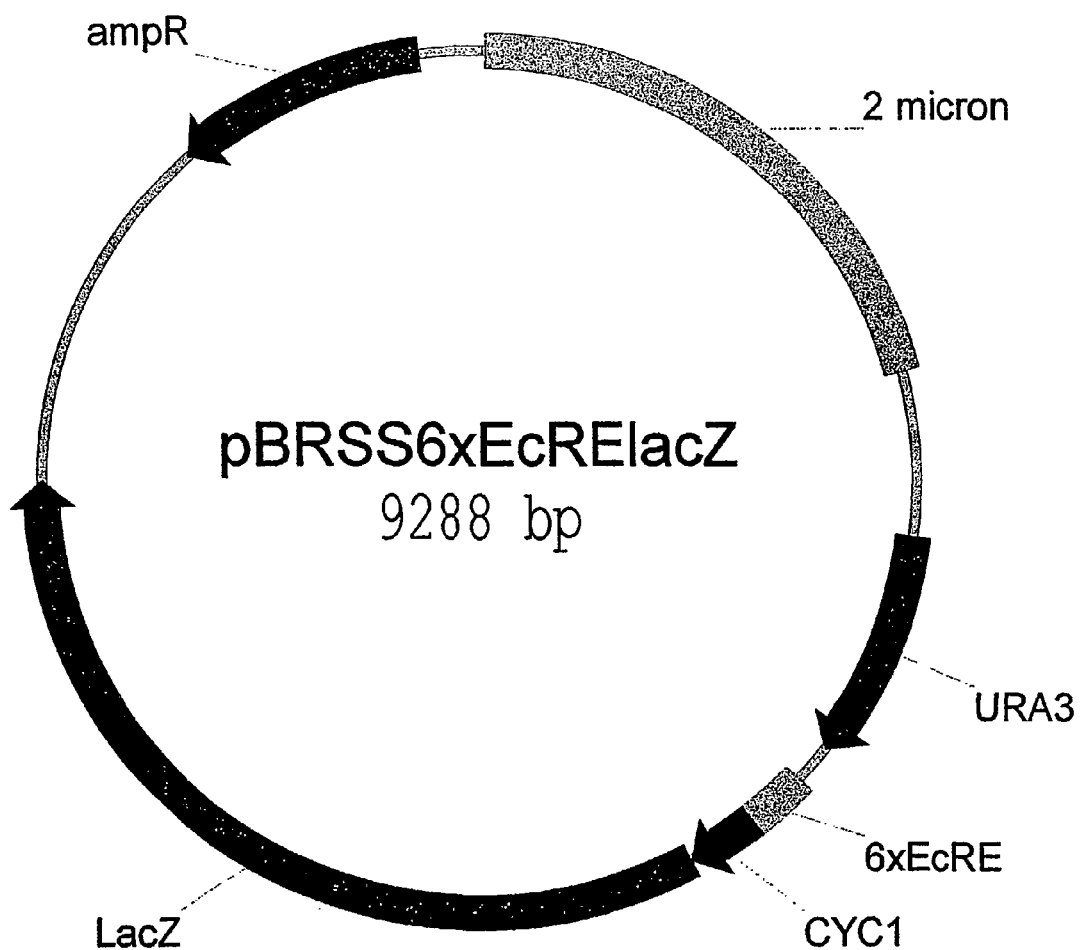
FIG. 2 is a schematic diagram of the LacZ-reporter gene with EcRE response elements. The yeast reporter plasmid, pBRSS 6× EcRE-lacZ, contains 6 copies of ecdysone reponse element derived from the *D. melanogaster* hsp27 heat shock protein gene (15) located upstream of the iso-1-cytochrome c (CYC1) promoter which is coupled to the *E. coli* beta-galactosidase gene (lacZ). This yeast-*E. coli* multicopy shuttle plasmid contains URA3 as a yeast transformation marker.
Figure 3B:
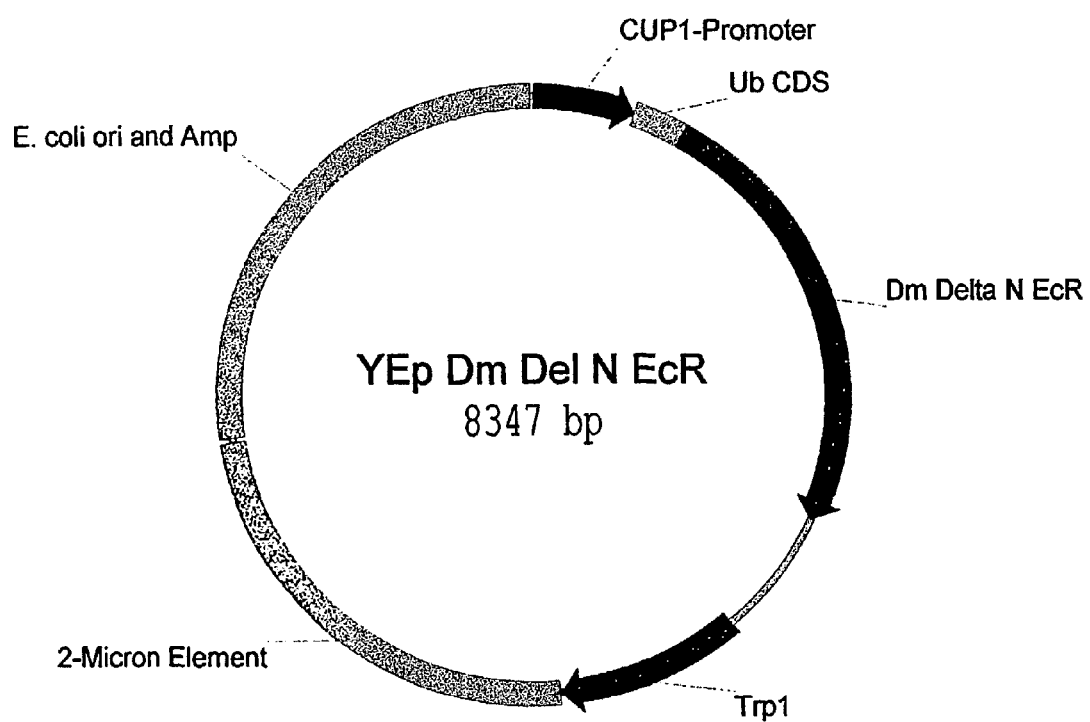
FIG. 3B shows YEp Dm ΔN EcR, the yeast expression plasmid encoding the N-terminal truncated *D. melanogaster* EcR B-1 ecdysone receptor. The first 220 amino acids up to VNSSISS sequence (SEQ ID NO: 25) have been deleted and the resulting sequence is inserted into the yeast expression vector to produce a ubiquitin (UBI) -fusion protein under the control of a CUP1 promoter. The A/B (AF-1) domain of EcR has been partially deleted in this construct. TRP1 is the tryptophan selectable marker and 2μm facilitates replication in yeast.
Figure 4A:
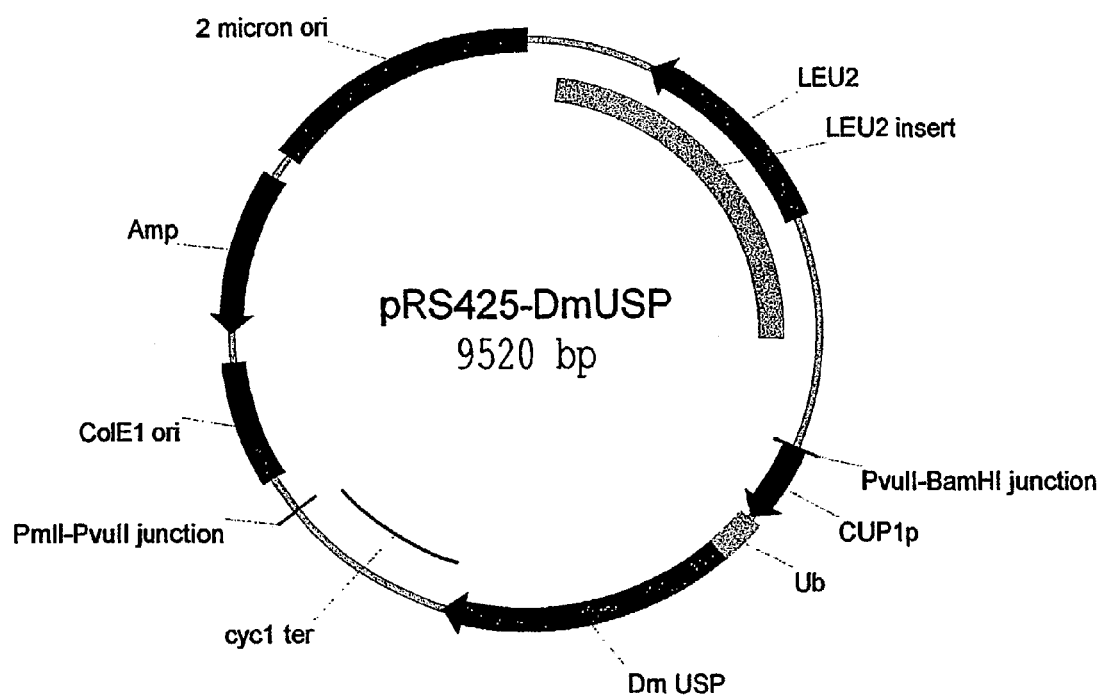
FIGS. 4A (pRS425-DmUSP) and 4B (pRS425-Dm ΔAB USP) show the yeast expression plasmids for expressing the *D. melanogaster* (DmUSP) receptor and variants thereof.
Figure 4B:
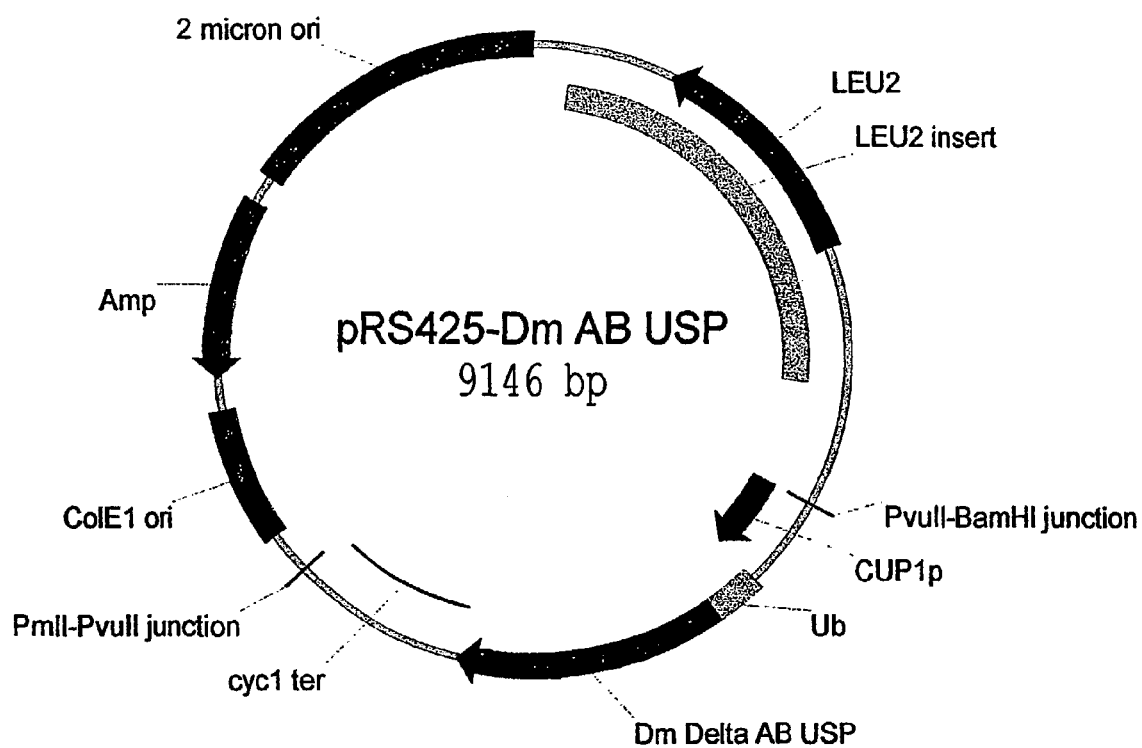
FIG. 4B shows the yeast expression plasmid for expressing DmUSP receptor wherein the N-terminal A/B domain, i.e., the first 90 amino acids up to YPPNH (SEQ ID NO: 26), have been deleted. The resulting construct is inserted into the yeast expression vector to produce a ubiquitin (UBI)-fusion protein under the control of a CUP1 promoter. LEU2 is the leucine (LEU2) selectable marker and 2μm facilitates replication in yeast.

Constitutive and Ligand Dependent Transactivation in Yeast Cells Expressing *D. melanogaster* Based DNA Constructs Using the transformation method set forth above, yeast were co-transformed with a reporter gene as shown in FIG. 2 and the expression vector encoding the full-length *D. melanogaster* ecdysone receptor, DmEcR (FIG. 3A) in the presence or absence of the Dm EcR heterodimer partner, DmUSP (FIG. 4A). Transformed cells were incubated with DMSO alone as a control or with a proprietary ecdysone receptor ligand (Rohm & Haas compound RH5992— tebufenozide) at final concentration 10 µM for 4 hours. The samples were then assayed for β-galactosidase activity as described above. Expression of the full-length Dm EcR consistently resulted in constitutive transactivation of the reporter gene, β-galactosidase. As the N-terminal portion of the Dm EcR receptor is reported to play a role in ligand independent transactivation, an expression vector containing an N-terminal deletion in the EcR was constructed (see FIG. 3B) and assessed in the β-galactosidase assays described above. Surprisingly, expression of DmEcR containing an N-terminal deletion did not constitutively transactivate the reporter gene regardless of whether the DmUSP was present or absent. Additionally, the EcR ligand RH 5992 (tebufenozide) was incapable of transactivating the reporter gene using these constructs. Restoration of ligand dependent transactivation was observed only when the DmΔN EcR, DmUSP and co-activator GRIP1 were coexpressed. See Table I. The data obtained indicate that the efficiency of ligand-dependent transactivation of the ecdysone receptor requires both heterodimer formation between EcR and USP, and proper interaction with co-activator GRIP1. In order to assess whether the mammalian homologues of USP, i.e., the retinoid receptors, RXRα or RXRβ, RXRγ, could substitute for the USP in these assays, we replaced the expression vector for Dm USP with expression vectors encoding these receptor homologues. We also tested additional insect USP, such as mosquito *A. aegypti* USP a- or b-form, spruce bud worm (Cf) USP (full-length and ΔA/B USP). In all cases tested, ligand-dependent transactivation was observed only when the co-activator GRIP1 was present. Superior results for ligand dependent transactivation of the DmEcR receptor were observed when the DmΔN EcR was combined with *A. aegypti* USP a or b form. See Table 1.

TABLE 1

| Receptors, co-activator | β-galactosidase activity | |
|---|---|---|
|  | DMSO | RH 5992 |
| Dm EcR-B1 | 1.090 | 1.200 |
| Dm EcR + DmUSP | 2.091 | 1.953 |
| Dm ΔN EcR + DmUSP | 0.152 | 0.182 |
| Dm ΔN EcR + DmUSP + GRIP1 | 0.424 | 2.537 |
| Dm ΔN EcR + RXRγ + GRIP1 | 0.364 | 1.283 |
| Dm ΔN EcR + Dm ΔA/B USP + GRIP1 | 0.340 | 2.323 |
| Dm ΔN EcR + Cf USP + GRIP1 | 1.149 | 1.409 |
| Dm ΔN EcR +Cf ΔA/B USP + GRIP1 | 0.235 | 0.590 |
| Dm ΔN EcR +Aa USPa-form + GRIP1 | 0.243 | 1.860 |
| Dm ΔN EcR +Aa USPb-form + GRIP1 | 0.251 | 2.068 |

EXAMPLE II

Figure 8A:
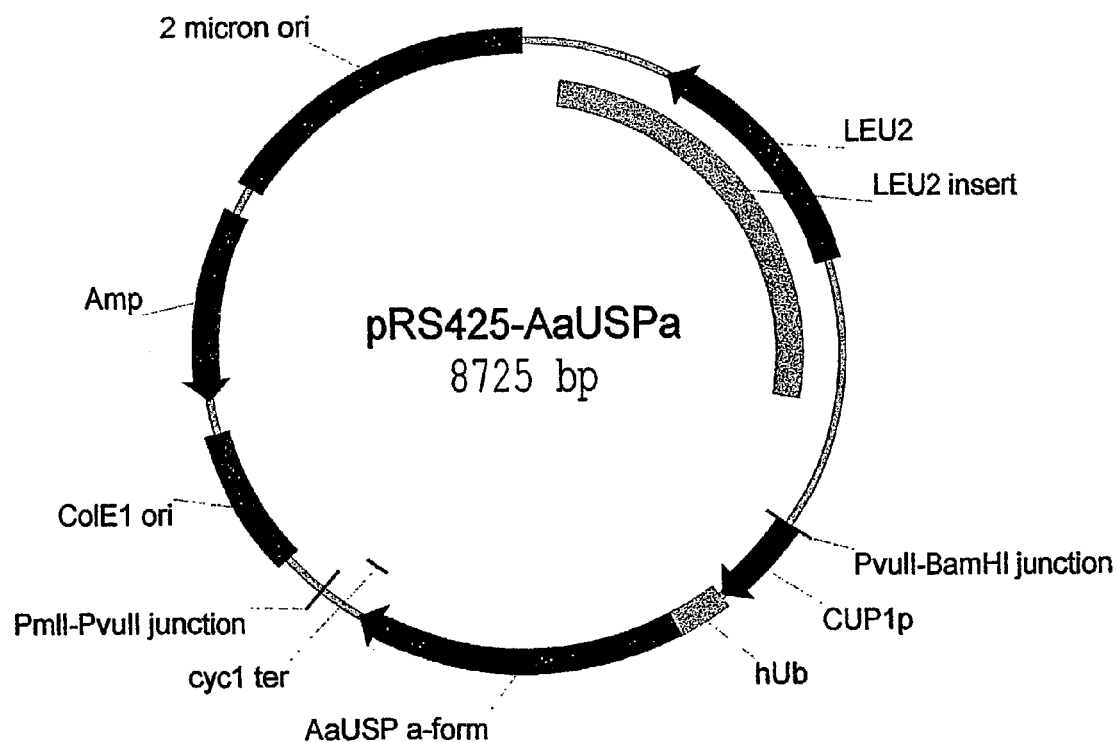
FIGS. 8A (pRS425AaUSPa), 8B (pRS425AaUSPb) and 8C (pRS425 Aa ΔAB USP) depict plasmids for expressing the *A. aegypti* USP a-form, b-form and an AB domain truncation mutant, respectively.
Figure 8B:
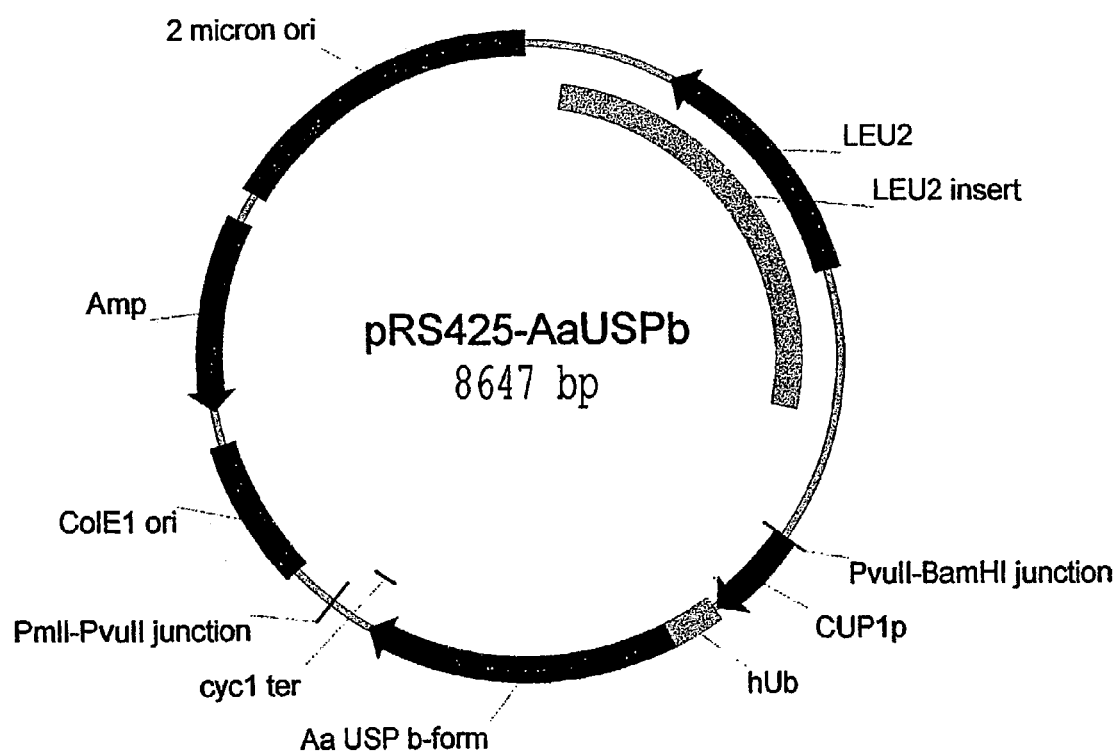
FIG. 8B shows a yeast expression plasmid encoding the full-length AaUSP b-form receptor. The mosquito *A. aegypti* USP b-form coding sequence is inserted into the yeast expression vector to produce a ubiquitin (UBI)-fusion protein under the control of a CUP1 promoter. LEU2 is the leucine selectable marker and 2μ facilitates replication in yeast.
Figure 8C:
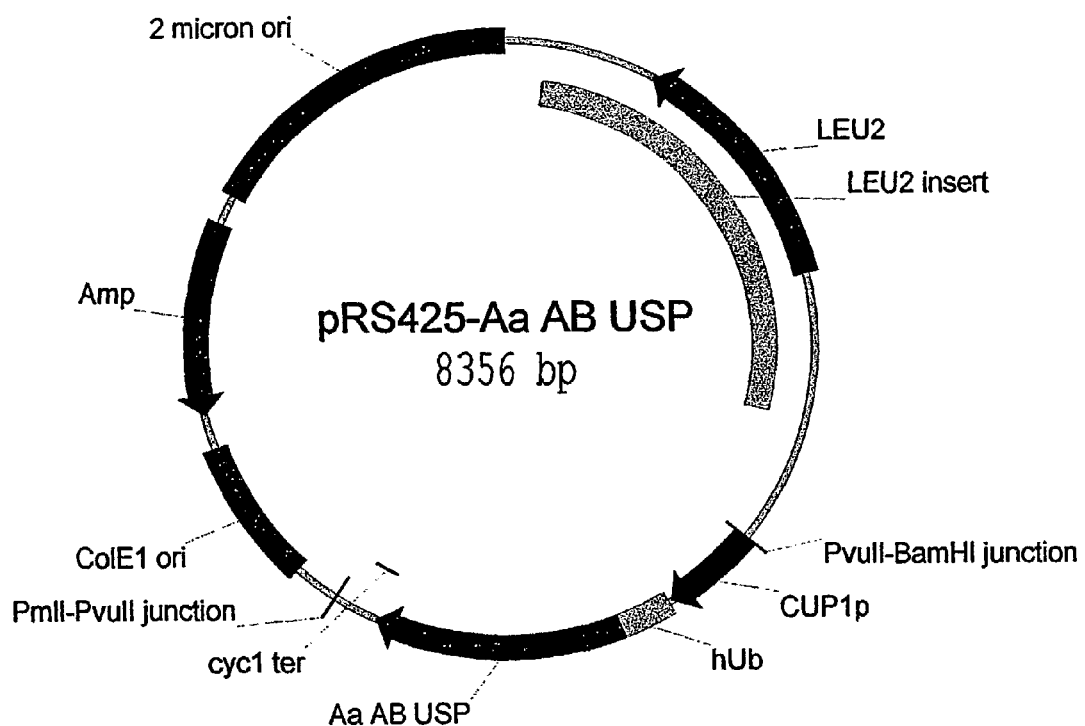
FIG. 8C shows an AaUSP truncation mutant wherein the N-terminal A/B domain, i.e, the first 124 amino acids of the USP a-form up to the YPPNH sequence (SEQ ID NO: 26), have been deleted. This sequence is common for both a- and b- forms of the USP receptor. The truncated mosquito *A. aegypti* USP receptor coding sequence is inserted into the yeast expression vector to produce a ubiquitin (UBI)-fusion protein under the control of a CUP1 promoter. LEU2 is the leucine selectable marker and 2μ facilitates replication in yeast.
Figure 9:
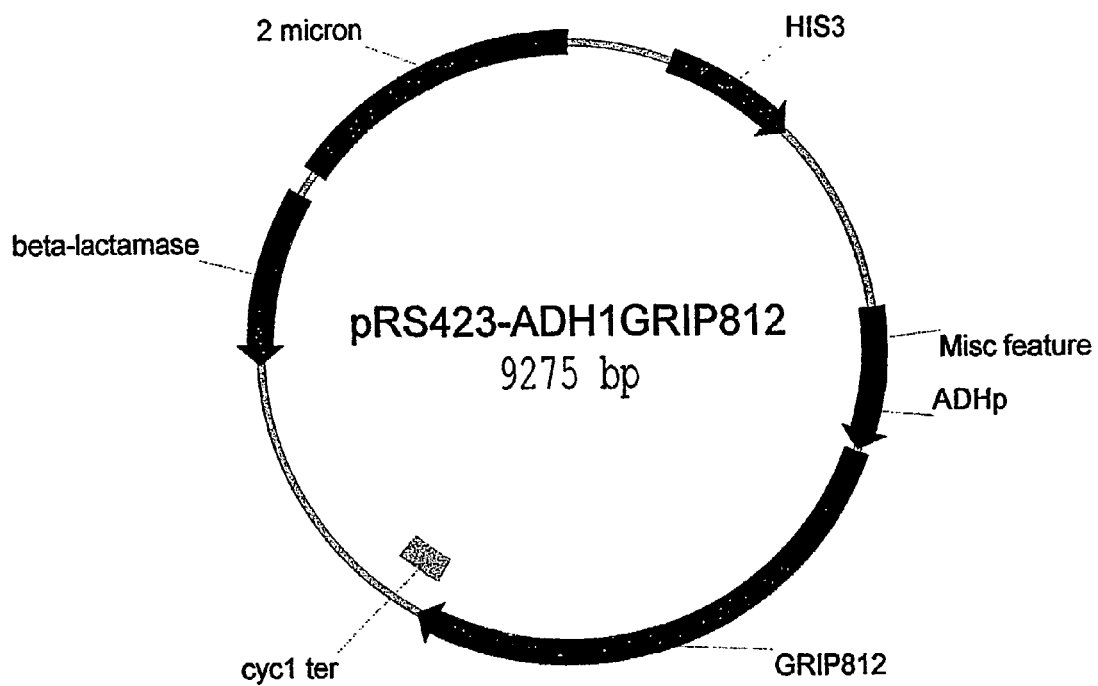
FIG. 9 shows a plasmid (pRS423-ADH1GRIP812) which encodes GRIP1. The GRIP1 gene, fused with ADH1 promoter (8) was cloned into the yeast-*E. coli* replicative plasmid pRS423 (17). HIS3 is the histidine selectable marker and 2μ facilitates replication in yeast.

Constitutive and Ligand Dependent Transactivation in Yeast Cells Expressing *Aedes aegypti* Based DNA Constructs Using the transformation method described above, yeast were co-transformed with a reporter gene as shown in FIG. 2 and the expression vector encoding the full-length *Aedes aegypti* ecdysone receptor, Aa EcR (FIG. 7A) in the presence or absence of the Aa EcR heterodimer partner, Aa USP (a or b form, FIGS. 8A and 8B respectively). Transformed cells were incubated with DMSO alone as a control, or with a proprietary ecdysone receptor ligand (Rohm & Haas tebufenozide[RH5992]) at final concentration 10 μM for 4 hours. The samples were then assayed for β-galactosidase activity as described above. Similar to the results presented in Example I with the full-length *D. melanogaster* ecdysone receptor, expression of the full-length AaEcR alone or in conjunction with AaUSP, consistently resulted in constitutive transactivation of the reporter gene. As the N-terminal portion of the AaEcR receptor is reported to play a role in ligand independent transactivation, an expression vector containing an N-terminal deletion in the Aa EcR was constructed (see FIG. 7B) and assessed in the β-galactosidase assays described above. Surprisingly, expression Aa EcR containing an N-terminal deletion did not constitutively transactivate the reporter gene regardless of whether the Aa USP was present or absent. Additionally, the EcR ligand RH5992 (tebufenozide) was incapable of transactivating the reporter gene with these constructs. Restoration of ligand dependent transactivation was observed only when the AaΔN EcR, AaUSP (a or b forms) and co-activator GRIP1 were coexpressed. See Table 2. As in the Drosophila system, the data obtained indicate that the efficiency of ligand-dependent transactivation of the ecdysone receptor in mosquito *A. aegypti* is dependent on the both heterodimer formation of EcR/USP and also upon proper interaction with co-activator GRIP1.

In order to assess whether the mammalian homologues of USP, i.e., the retinoid receptors, RXRα or RXRβ, RXRγ, could substitute for the AaUSP in these assays, we replaced the expression vector for Aa USP with expression vectors encoding these receptor homologues. We also tested additional insect USP, such as *Aedeses aegypti* USP a- or b-form, spruce bud worm (Cf) USP (full-length and ΔA/B USP). In all cases tested, ligand dependent transactivation was observed only when the co-activator GRIP1 was present. Superior results for ligand dependent transactivation of the mosquito *A. aegypti* EcR receptor system were observed when the Aa ΔA/B EcR was combined with spruce bud worm Cf ΔA/B USP in the presence of GRIP1. See Table 2.

TABLE 2

| Receptors, co-activator | β-galactosidase activity | |
|---|---|---|
|  | DMSO | RH 5992 |
| Aa EcR | 2.500 | 2.750 |
| Aa USPa | 0.210 | 0.223 |
| Aa USPb | 0.196 | 0.210 |
| Aa EcR + Aa USPa | 2.300 | 2.453 |
| Aa EcR + Aa USPb | 3.000 | 2.700 |
| Aa ΔA/B EcR + Aa USPa | 0.194 | 0.209 |
| Aa ΔA/B EcR + Aa USPb | 0.177 | 0.184 |
| Aa ΔA/B EcR + Aa ΔA/B USP | 0.187 | 0.196 |
| Aa ΔA/B EcR + Aa USPa + GRIP1 | 0.272 | 2.026 |
| Aa ΔA/B EcR + AaUSPb + GRIP1 | 0.240 | 2.074 |
| Aa ΔA/B EcR + Aa ΔA/B USP + GRIP1 | 0.194 | 1.370 |
| Aa ΔA/B EcR + Cf ΔA/B USP + GRIP1 | 0.250 | 3.000 |
| Aa ΔA/B EcR + RXRα + GRIP1 | 0.544 | 2.032 |
| Aa ΔA/B EcR + RXRβ + GRIP1 | 0.231 | 1.983 |
| Aa ΔA/B EcR + RXRγ + GRIP1 | 0.496 | 2.666 |

EXAMPLE III

Figure 6A:
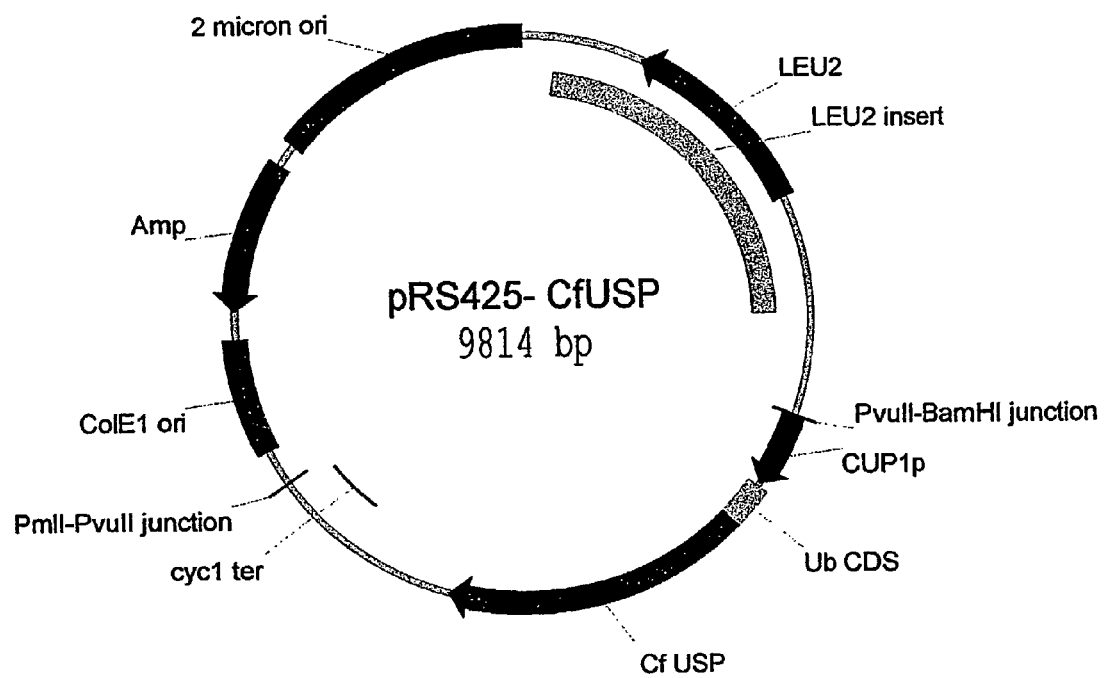
FIGS. 6A (pRS425CfUSP) and 6B (pRS425Cf ΔAB USP) show plasmids which express the full-length spruce budworm, *C. fumiferana* CfUSP receptor and a CfUSP containing an N-terminal deletion.
Figure 6B:
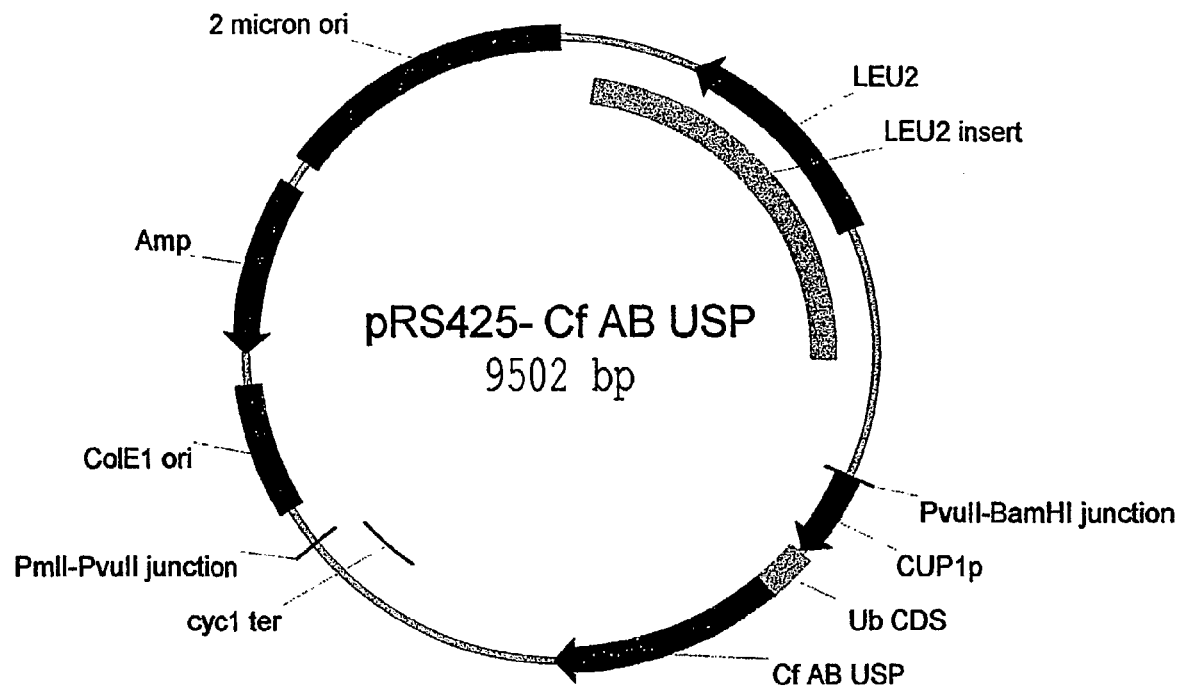
FIG. 6B shows the yeast expression plasmid for expressing spruce budworm, CfUSP receptor wherein the N-terminal A/B domain, i.e., the first 105 amino acids up to YPPNH, have been deleted. The resulting construct is inserted into the yeast expression vector to produce a ubiquitin (UBI)-fusion protein under the control of a CUP1 promoter. LEU2 is the leucine (LEU2) selectable marker and 2 μm facilitates replication in yeast.

Constitutive and Ligand Dependent Transaction in Yeast Cells Expressing *Choristoneura fumiferana* Based DNA Constructs Using the transformation method described above, yeast were co-transformed with a reporter gene as shown in FIG. 2 and the expression vector encoding the full-length *Choristoneura fumiferana* ecdysone receptor, Cf EcR (FIG. 5A) in the presence or absence of the Cf EcR heterodimer partner, Cf USP (FIG. 6A). Transformed cells were incubated with DMSO alone as a control, or with a proprietary ecdysone receptor ligand (Rohm & Haas RH5992) at final concentration 10 μM for 4 hours. The samples were then assayed for β-galactosidase activity as described above. In contrast to the results presented in Examples I and II with the full-length *D. melanogaster* and mosquito *A. aegypti* ecdysone receptors, expression of the full-length CfEcR alone did not constitutively transactivate the reporter gene. See Table 3. Expression of the Cf USPR alone also did not constitutively activate the reporter gene, consistent with the results for mosquito *A. aegypti* presented in Table 2. However, as with all systems tested, fruit fly, mosquito and spruce bud worm, co-expression of CfEcR with CfUSP did give rise to constitutive transactivation of reporter gene. See Table 3. Surprisingly, co-expression of Cf ΔA/B EcR, i.e., CfEcR with deletion of the entire AF-1 domain, with CfUSP, also resulted in strong constitutive transactivation. However, deletion of the A/B domain of the CfUSP abolished this constitutive transactivation of the reporter gene. Thus, in the spruce bud worm system, constitutive transcription is not observed when CfEcR/Cf ΔAB USP or Cf ΔAB EcR/Cf ΔAB USP are co-expressed. These data suggest that the AF-1 domain of the Cf USP, in cooperation with Cf EcR possesses ligand-independent transactivation activity. Ligand dependent transactivation was observed only in the presence of the co-activator GRIP1. We also observed stronger ligand dependent activity for the Cf ΔA/B EcR+Cf ΔA/B USP+GRIP1 combination than the CfEcR+CfΔA/B USP+GRIP1 combination. These results suggest that the AF-1 domain of CfEcR may possess repressor activity.

TABLE 3

| Receptors, co-activator | β-galactosidase activity | |
|---|---|---|
| | DMSO | RH 5992 |
| Cf EcR | 0.201 | 0.175 |
| Cf USP | 0.233 | 0.230 |
| Cf EcR + CfUSP | 2.734 | 3.000 |
| Cf ΔA/B EcR + Cf USP | 2.684 | 3.000 |
| Cf EcR + Cf ΔA/B USP | 0.205 | 0.241 |
| Cf ΔA/B EcR + Cf ΔA/B USP | 0.209 | 0.234 |
| Cf EcR + Cf ΔA/B USP + GRIP1 | 0.223 | 0.492 |
| Cf ΔA/B EcR + Cf ΔA/B USP + GRIP1 | 0.200 | 2.500 |
| Cf ΔA/B EcR + RXR α + GRIP1 | 0.270 | 2.063 |
| Cf ΔA/B EcR + RXR β + GRIP1 | 0.205 | 0.456 |
| Cf ΔA/B EcR + RXR γ + GRIP1 | 0.200 | 1.030 |

In order to assess the transactivation activity of the USP receptor mammalian homologues in the spruce bud worm system, we also replaced the Cf ΔAB USP in the Cf ΔAB EcR+Cf ΔAB USP+GRIP1 combination with the following receptors, RXRα, RXRβ and RXRγ, as set forth in Table 3. USP from other insects such as from *D. melanogaster* and mosquito *A. aegypti* were also tested (data not shown). Although ligand dependent transactivation was observed with the retinoid X receptor, USP homologues, the strongest ligand dependent transactivation was observed for the Cf ΔAB EcR+Cf ΔAB USP+GRIP1 combination.

EXAMPLE IV

Method for Modulating Expression of a Gene of Interest in a Host in a Ligand-Dependent Manner In examples I, II and III we have described systems wherein expression of a reporter gene fused to the ecdysone inducible promoter can be up-regulated in ligand dependent manner using *Drosophila melanogaster*, or *Aedes aegypti* or *Choristoneura fumiferana* altered ecdysone receptors in combination with their partners insect USP or mammalian counterparts—RXR and the presence of co-activator GRIP. The expression of the reporter is induced by the addition of the ecdysone nuclear receptor ligands.

The foregoing system may be modified to express a gene of interest by coupling it with the ecdysone responsive promoter. For example, the open reading frame of the beta-gaclosidase may be replaced with the open reading frame of a human gene that encodes insulin. Alternatively, using the methods of the present invention, the expression of the reporter gene or a gene of interest could be kept on constitutively and then turned off by the addition ecdysone receptor ligands.

Figure 10A:
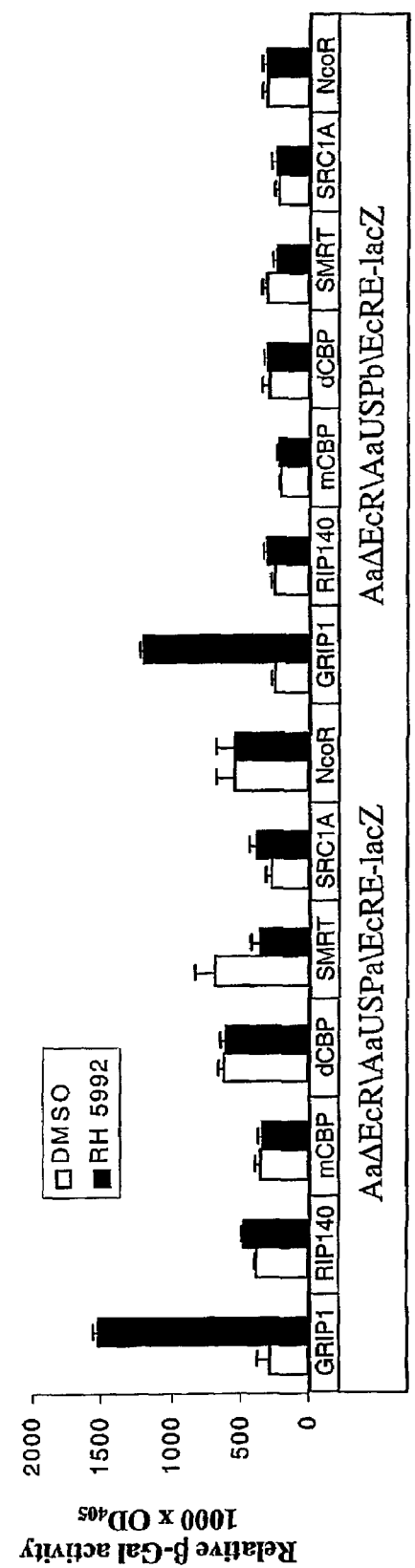
FIGS. 10A and 10B are graphs showing the roles of the coactivators and co-repressors in transactivation of AaΔEcR. Interaction of different transcriptional factors in combination with the heterodimers AaΔEcR/USPa or AaΔEcR/USPb (FIG. 10A).
Figure 10B:
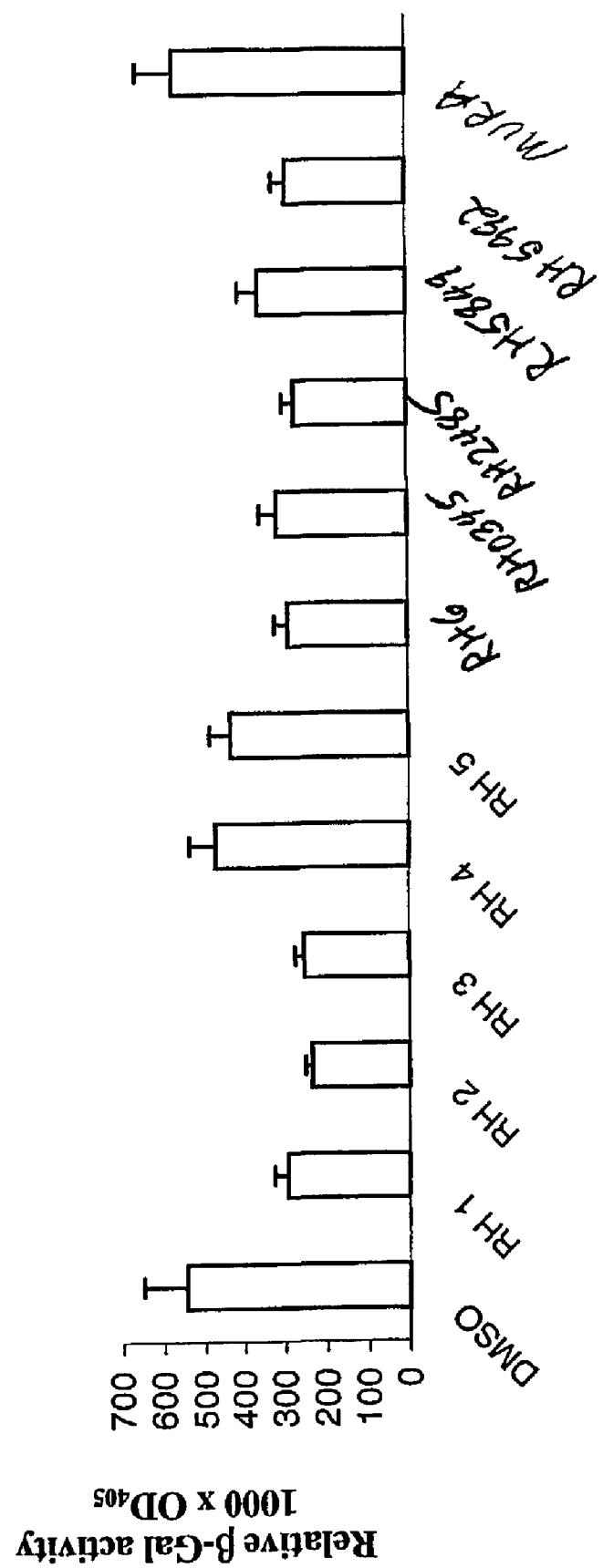

Using the transformation method described above, yeast were co-transformed with a reporter gene as shown in FIG. 2 and the expression vectors encoding *A. aegypti* AB ΔEcR and *A. aegypti* USP-a or USP-b isoforms. The yeast expression vectors for expression of different co-activators such Drosophila CBP (Akimaru et al. 1997; Nature 386:735–738), mouse CBP (Chrivia et al. 1993; Nature 365:855–859), GRIP1 (Hong et al. 1996; ), SRC-1 (Onate et al. 1995), RIP140 (Cavailles et al. 1995; EMBO J. 14:3741–3751), SMRT (Chen et al. 1996; PNAS 93:7567–7571), and NcoR (Horlein et al. 1995; Nature 377:397–404) were also introduced to the host. As presented in FIG. 10A, addition of the SMRT co-activator gave rise to an increase of expression of the reporter gene in the absence of ligands. Addition of ligands, however, such as RH 5992 at a concentration of 10 μM resulted in suppression of the levels of reporter gene expression. Thus, in the current system, constitutive transcription of the reporter is observed when Aa AB EcR/Aa USPa and SMRT are co-expressed. The addition of cognate ligands to the system reduces expression of the reporter indicating that SMRT possesses repressor activity. This property may be used to advantage in methods for the ligand-dependent down regulation of gene expression.

EXAMPLE V

Method to Eliminate Constitutive Transcriptional Activity or Repression Activity of Nuclear Receptors As mentioned previously, most nuclear receptors possess similar domain structures in that they contain six recognizable homologous domains termed A/B, C, D, E and F. These domains have been found to possess the following functions: ligand-independent transcriptional function (A/B), ligand-dependent transcriptional function (E), DNA binding (C), steroid binding (E), nuclear localization (D), and dimerization (E). Deletion or mutation of the A/B domain does not affect ligand-dependent transactivation, dimerization and ligand binding activity. We have demonstrated herein that for both nuclear receptors with known ligands (for example, ecdysone receptors) and for orphan receptors (for example, ultraspiracle USP), mutation of the A/B domain, including, but not limited to deletion of the A/B domain, abolishes constitutive transcriptional activity, making the system more responsive to ligand activation.

TABLE 4

| Receptors, co-activator | β-galactosidase activity | |
|---|---|---|
| | DMSO | RH 5992 |
| Dm EcR-B1 | 1.090 | 1.200 |
| Dm EcR + DmUSP | 2.091 | 1.953 |
| Dm ΔN EcR + DmUSP | 0.152 | 0.182 |
| Dm ΔN EcR + DmUSP + GRIP1 | 0.424 | 2.537 |
| Aa EcR | 2.500 | 2.750 |
| Aa EcR + Aa USPa | 2.300 | 2.453 |
| Aa EcR + Aa USPb | 3.000 | 2.700 |
| Aa ΔA/B EcR + Aa USPa | 0.194 | 0.209 |
| Aa ΔA/B EcR + Aa USPb | 0.177 | 0.184 |
| Aa ΔA/B EcR + Aa USPa + GRIP1 | 0.272 | 2.026 |
| Aa ΔA/B EcR + Aa USPb + GRIP1 | 0.240 | 2.074 |
| Cf EcR + CfUSP | 2.734 | 3.000 |
| Cf ΔA/B EcR + Cf USP | 2.684 | 3.000 |
| Cf EcR + Cf ΔA/B USP | 0.205 | 0.241 |
| Cf ΔA/B EcR + Cf ΔA/B USP | 0.209 | 0.234 |
| Cf EcR + CfΔA/B USP + GRIP1 | 0.223 | 0.492 |
| Cf ΔA/B EcR + CfΔA/B USP + GRIP1 | 0.200 | 3.000 |

Expression of DmEcR or AaEcR resulted in ligand-independent transactivation of the reporter gene. The constitutive transcription activity is eliminated when the A/B domain of the DmEcR or AaEcR is deleted. Co-expression of CfEcR with CfUSP (CfEcR:CfUSP heterodimer) leads to constitutive transcription of the reporter gene. The activity is eliminated only when the A/B domain of the orphan receptor CfUSP is deleted. The complex CfEcR:CfΔA/B USP:GRIP1 is responsive, but not very sensitive to a ligand (RH5992), the system becomes more responsive when the A/B domain of the CfEcR is truncated. In all the systems examined, abolition the function of the A/B domain in the nuclear receptors (EcR) or orphan receptors (USP) did not reduce but enhanced a response to a ligand.

REFERENCES

1. Allegretto, E. A., M. R. McClurg, S. B. Lazarchik, D. L. Clemm, S. A. Kerner, M. G. Elgort, M. P. Boehm, S. K. White, J. W. Pike, and R. A. Heyman. 1993. Transactivation properties of retinoic acid and retinoid X receptors in mammalian cells and yeast. Correlation with hormone binding and effects of metabolism [published erratum appears in J Biol Chem 1994 Mar 11;269(10):7834]. J Biol Chem 268:26625–33.
2. Bachmair, A., D. Finley, and A. Varshavsky. 1986. In vivo half-life of a protein is a function of its amino-terminal residue. Science 234:179–86.
3. Baker, R. T. 1996. Protein expression using ubiquitin fusion and cleavage. Curr Opin Biotechnol 7:541–6.
4. Beato, M., G. Chalepakis, M. Schauer, and E. P. Slater. 1989. DNA regulatory elements for steroid hormones. J Steroid Biochem 32:737–47.
5. Cho, W., M. Kapitskaya, and A. Raikhel. 1994. Mosquito ecdysteroid receptor: Analysis of the cDNA and expression during vitellogenesis. Insect. Biochem. Mol. Biol. 25:19–27.
6. Graumann, K., J. L. Wittliff, W. Raffelsberger, L. Miles, A. Jungbauer, and T. R. Butt. 1996. Structural and functional analysis of N-terminal point mutants of the human estrogen receptor. J Steroid Biochem Mol Biol 57:293–300.
7. Henrich, V. C., T. J. Sliter, D. B. Lubahn, A. MacIntyre, and L. I. Gilbert. 1990. A steroid/thyroid hormone receptor superfamily member in *Drosophila melanogaster* that shares extensive sequence similarity with a mammalian homologue. Nucleic Acids Res 18:4143–8.
8. Hong, H., K. Kohli, A. Trivedi, D. L. Johnson, and M. R. Stallcup. 1996. GRIP1, a novel mouse protein that serves as a transcriptional coactivator in yeast for the hormone binding domains of steroid receptors. Proc Natl Acad Sci U S A 93:4948–52.
9. Ignar-Trowbridge, D. M., M. Pimentel, M. G. Parker, J. A. McLachlan, and K. S. Korach. 1996. Peptide growth factor cross-talk with the estrogen receptor requires the A/B domain and occurs independently of protein kinase C or estradiol. Endocrinology 137:1735–44.
10. Kapitskaya, M., S. Wang, D. E. Cress, T. S. Dhadialla, and A. S. Raikhel. 1996. The mosquito ultraspiracle homologue, a partner of ecdysteroid receptor heterodimer: cloning and characterization of isoforms expressed during vitellogenesis. Mol Cell Endocrinol 121:119–32.
11. Koelle, M. R., W. S. Talbot, W. A. Segraves, M. T. Bender, P. Cherbas, and D. S. Hogness. 1991. The *Drosophila* EcR gene encodes an ecdysone receptor, a new member of the steroid receptor superfamily. Cell 67:59–77.
12. Kothapalli, R., S. R. Palli, T. R. Ladd, S. S. Sohi, D. Cress, T. S. Dhadialla, G. Tzertzinis, and A. Retnakaran. 1995. Cloning and developmental expression of the ecdysone receptor gene from the spruce budworm, *Choristoneura fumiferana*. Dev Genet 17:319–30.
13. Perera, S. C., S. R. Palli, T. R. Ladd, P. J. Krell, and A. Retnakaran. 1998. The ultraspiracle gene of the spruce budworm, *Choristoneura fumiferana*: cloning of cDNA and developmental expression of mRNA. Dev Genet 22:169–79.
14. Perera, S. C., M. Sundaram, P. J. Krell, A. Retnakaran, T. S. Dhadialla, and S. R. Palli. 1999. An analysis of ecdysone receptor domains required for heterodimerization with ultraspiracle [In Process Citation]. Arch Insect Biochem Physiol 41:61–70.
15. Riddihough, G., and H. Pelham. 1987. An ecdysone response element in the *Drosophila melanogaster*. EMBO J. 21:181–197.
16. Schena, M., and K. R. Yamamoto. 1988. Mammalian glucocorticoid receptor derivatives enhance transcription in yeast. Science 241:965–7.
17. Sikorski, R. S., and P. Hieter. 1989. A system of shuttle vectors and yeast host strains designed for efficient manipulation of DNA in *Saccharomyces cerevisiae*. Genetics 122:19–27.
18. Stack, G., V. Kumar, S. Green, M. Ponglikitmongkol, M. Berry, M. C. Rio, A. M. Nunez, M. Roberts, C. Koehl, P. Bellocq, and et al. 1988. Structure and function of the pS2 gene and estrogen receptor in human breast cancer cells. Cancer Treat Res 40:185–206.
19. Suhr, S. T., E. B. Gil, M. C. Senut, and F. H. Gage. 1998. High level transactivation by a modified *Bombyx* ecdysone receptor in mammalian cells without exogenous retinoid X receptor. Proc Natl Acad Sci U S A 95:7999–8004.
20. Thomas, H. E., E. G. Stunnenberg, and A. F. Stewart. 1993. Heterodimerization of the *Drosophila ecdysone* receptor with retinoid X receptor and ultraspiracle. Nature 362:471–5.
21. Yao, T. P., B. M. Forman, Z. Jiang, L. Cherbas, J. D. Chen, M. McKeown, P. Cherbas, and R. M. Evans. 1993. Functional ecdysone receptor is the product of EcR and Ultraspiracle genes. Nature 366:476–9.
22. Yao, T. P., W. A. Segraves, A. E. Oro, M. McKeown, and R. M. Evans. 1992. *Drosophila ultraspiracle* modulates ecdysone receptor function via heterodimer formation. Cell 71:63–72.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A ligand dependent transactivation system for screening insecticidal compounds, comprising:
   a) a first DNA construct having a nucleic acid molecule encoding an altered ecdysone receptor operably linked to a promoter, wherein said altered ecdysone receptor is an ecdysone receptor with a deleted A/B domain;
   b) a second DNA construct having a nucleic acid molecule encoding a receptor which heterodimerizes with said ecdysone receptor upon transactivation, said nucleic acid molecule being operably linked to a promoter, wherein said receptor is selected from the group consisting of insect ultraspiracle gene product (USP) receptors and mammalian retinoid X receptors (RXR);
   c) a third DNA construct comprising a promoter containing a plurality of ecdysone response elements, said promoter being operably linked to a reporter gene;
   d) a fourth DNA construct encoding a co-activator molecule, said co-activator molecule being operably linked to a promoter sequence; and
   e) a host cell comprising said first, second, third and fourth DNA constructs, expression of said reporter gene being dependent upon ligand dependent transactivation effectuated by said insecticidal compound.

2. A system as claimed in claim 1, wherein said insect USP receptors is selected from the group consisting of USP, USP a form, USP b form, and ΔA/B USP.

3. A system as claimed in claim 1, wherein said co-activator molecule is selected from the group consisting of GRIP 1, SRC1, p/CIP and the homologues of mammalian GRIP and SRC1.

4. A system as claimed in claim 1, wherein at least one of said promoters in step a), b), c), or d) is an inducible promoter selected from the group consisting of CUP1, HSP70, β-galactose-inducible promoters, GAL1, and GAL10.

5. A system as claimed in claim 1, wherein at least one of said promoters in step a), b), c), or d) is a constitutive promoter selected from the group consisting of ADH1 and GPD.

6. A system as claimed in claim 1, wherein said first, second, third and fourth DNA constructs are each contained within a first, second, third and fourth expression vector, said expression vectors containing sequences which enable replication in both yeast and E. coli.

7. A system as claimed in claim 1, said first and second DNA constructs containing nucleic acid sequences isolated from D. melanogaster.

8. A system as claimed in claim 1, said first DNA construct containing a nucleic acid sequence isolated from *D. melanogaster*, said second DNA construct containing a nucleic acid sequence isolated from mosquito *A. aegypti*.

9. A system as claimed in claim 1, said first and second DNA constructs containing nucleic acid sequences isolated from *A. aegypti*.

10. A system as claimed in claim 1, said first DNA construct containing a nucleic acid sequence from mosquito *A. aegypti*, said second DNA construct containing a nucleic acid sequence encoding a receptor selected from the group consisting of CfUSP receptor and human retinoid X receptor.

11. A system as claimed in claim 1, said first and second DNA constructs containing nucleic acid sequences isolated from *C. fumiferana*.

12. A system as claimed in claim 1, said first DNA construct containing a nucleic acid sequence from *C. fumiferana* and said second DNA construct containing a nucleic acid sequence encoding a receptor selected from the group consisting of retinoid X receptor α and retinoid X receptor γ.

13. A system as claimed in claim 1, wherein said host cell is a yeast cell.

14. A system as claimed in claim 13, wherein said yeast is *Saccharomyces cerevisiae*.

15. A system as claimed in claim 1, wherein said reporter gene is selected from the group consisting of β-galactosidase, β-glucuronidase, alkaline phosphatase, green fluorescent protein, and chloramphenicol acetyltransferase.

16. A system as claimed in claim 1, wherein said receptor which heterodimerizes with said ecdysone receptor is also altered, said alteration being selected from the group consisting of a truncation, an insertion, a partial deletion of a the A/B domain, a full deletion of the A/B domain, site-directed or randomly mutagenized A/B domain.

17. A system as claimed in claim 1, wherein said first DNA construct encodes an altered ecdysone receptor from *D. melanogaster*, said second DNA construct encodes a receptor which heterodimerizes with said ecdysone receptor, said heterodimerizing receptor being selected from the group consisting of USP from *D. melanogaster*, ΔA/B USP from *D. melanogaster*, ΔA/B USP from *C. fumiferana*, and retinoid X receptor γ, said reporter gene being β-galactosidase and said co-activator being GRIP 1.

18. A system as claimed in claim 1, wherein said first DNA construct encodes an altered ecdysone receptor from *A. aegypti*, said second DNA construct encodes a receptor which heterodimerizes with said ecdysone receptor, said heterodimerizing receptor being selected from the group consisting of USP a form from *A. aegypti*, USP b form from *A. aegypti*, ΔA/B USP from *A. aegypti*, ΔA/B USP from *C. fumiferana*, retinoid X receptor α, retinoid X receptor β, retinoid X receptor γ, said reporter gene being β-galactosidase and said co-activator being GRIP 1.

19. A system as claimed in claim 1, wherein said first DNA construct encodes an altered ecdysone receptor from *C. fumiferana*, said second DNA construct encodes a receptor which heterodimerizes with said ecdysone receptor, said heterodimerizing receptor being selected from the group consisting of ΔA/B USP from *C. fumiferana*, retinoid X receptor α, retinoid X receptor γ, said reporter gene being β-galactosidase and said co-activator being GRIP 1.

20. A method for identifying insecticidal compounds which transactivate nuclear receptors in a ligand-dependent manner, comprising:
a) providing a host cell containing:
(i) a first DNA construct having a nucleic acid molecule encoding an altered ecdysone receptor operably linked to a promoter, wherein said altered ecdysone receptor is an ecdysone receptor with a deleted A/B domain;
(ii) a second DNA construct having a nucleic acid molecule encoding a receptor which heterodimerizes with said altered ecdysone receptor upon transactivation, said nucleic acid molecule being operably linked to a promoter, wherein said receptor is selected from the group consisting of insect ultraspiracle gene product (USP) receptors and mammalian retinoid X receptors (RXR);
(iii) a third DNA construct comprising a promoter containing a plurality of ecdysone response elements, said promoter being operably linked to a reporter gene; and
(iv) a fourth DNA construct encoding a co-activator molecule, said co-activator molecule being operably linked to a promoter sequence;
b) contacting said host cell with an effective amount of a compound suspected to possess insecticidal activity;
c) assessing the level of ligand dependent co-activation mediated by said compound as indicated by expression levels of said reporter gene.

21. A method as claimed in claim 20, wherein said insect USP is selected from the group consisting of USP, USP a form, USP b form, and ΔA/B USP.

22. A method as claimed in claim 21, wherein said co-activator molecule is selected from the group consisting of GRIP 1, SRC1 and p/CIP.

23. A method as claimed in claim 20, wherein at least one of said promoters in step a), is an inducible promoter selected from the group consisting of CUP1, HSP70, galactose-inducible promoters, GAL1, and GAL10.

24. A method as claimed in claim 20, wherein at least one of said promoters in step a is a constitutive promoter selected from the group consisting of ADH and GPD.

25. A method as claimed in claim 20, wherein said first, second, third and fourth DNA constructs are each contained within a first, second, third and fourth expression vector, said expression vectors containing sequences which enable replication in both yeast and *E. coli*.

26. A method as claimed in claim 20, said first and second DNA constructs containing nucleic acid sequences isolated from *D. melanogaster*.

27. A method as claimed in claim 20, said first DNA construct containing a nucleic acid sequence isolated from *D. melanogaster*, said second DNA construct containing a nucleic acid sequence isolated from mosquito *A. aegypti*.

28. A method as claimed in claim 20, said first and second DNA constructs containing nucleic acid sequences isolated from *A. aegypti*.

29. A method as claimed in claim 20, said first DNA construct containing a nucleic acid sequence from mosquito *A. aegypti*, said second DNA construct containing a nucleic acid sequence encoding a receptor selected from the group consisting of CfUSP receptor and human retinoid X receptor.

30. A method as claimed in claim 20, said first and second DNA constructs containing nucleic acid sequences isolated from *C. fumiferana*.

31. A method as claimed in claim 20, said first DNA construct containing a nucleic acid sequence from *C. fumiferana* and said second DNA construct containing a nucleic acid sequence encoding a receptor selected from the group consisting of retinoid X acid receptor α and retinoid X receptor γ.

32. A method as claimed in claim 31, wherein said host cell is a yeast cell.

33. A method as claimed in claim 32, wherein said yeast is *Saccharomyces cerevisiae.*

34. A method as claimed in claim 20, wherein said reporter gene is selected from the group consisting of β-galactosidase, β-glucuronidase, alkaline phosphatase, green fluorescent protein, and chloramphenicol acetyltransferase.

35. A method as claimed in claim 20, wherein said receptor which heterodimerizes with said ecdysone receptor is also altered, said alteration being selected from the group consisting of a truncation, an insertion, a partial deletion of a the A/B domain, a full deletion of the A/B domain, site-directed, randomly mutagenized A/B domain.

36. A method as claimed in claim 20, wherein said first DNA construct encodes an altered ecdysone receptor from *Drosphila melanogaster,* said second DNA construct encodes a receptor which heterodimerizes with said ecdysone receptor, said heterodimerizing receptor being selected from the group consisting of USP from *D. melanogaster*, ΔA/B USP from *D. melanogaster,* ΔA/B USP from *C. fumiferana,* and retinoid X receptor γ, said reporter gene being β-galactosidase and said co-activator being GRIP 1.

37. A method as claimed in claim 20, wherein said first DNA construct encodes an altered ecdysone receptor from *A. aegypti,* said second DNA construct encodes a receptor which heterodimerizes with said ecdysone receptor, said heterodimerizing receptor being selected from the group consisting of USP a form from *A. aegypti,* USP b form from *A. aegypti,* ΔA/B USP from *A. aegypti,* ΔA/B USP from *C. fumiferana,* retinoid X receptor α, retinoid X receptor β, retinoid X receptor γ, said reporter gene being β-galactosidase and said co-activator being GRIP 1.

38. A method as claimed in claim 20, wherein said first DNA construct encodes an altered ecdysone receptor from *C. fumiferana,* said second DNA construct encodes a receptor which heterodimerizes with said ecdysone receptor, said heterodimerizing receptor being selected from the group consisting of ΔA/B USP from *C. fumiferana,* retinoid X receptor α, retinoid X receptor γ, said reporter gene being β-galactosidase and said co-activator being GRIP 1.

39. A method for regulating expression of a gene of interest in a host in a ligand-dependent manner, comprising:

a) providing a host cell comprising:

(i) a first DNA construct having a nucleic acid molecule encoding an altered ecdysone receptor operably linked to a promoter, wherein said altered ecdysone receptor is an ecdysone receptor with a deleted A/B domain;

ii) a second DNA construct having a nucleic acid molecule encoding a receptor which heterodimerizes with said ecdysone receptor upon transactivation, said nucleic acid molecule being operably linked to an promoter, wherein said receptor is selected from the group consisting of insect ultraspiracle gene product (USP) receptors and mammalian retinoid X receptors (RXR);

iii) a third DNA construct comprising a promoter containing a plurality of ecdysone response elements, said promoter being operably linked to a gene of interest; and iv) a fourth DNA construct encoding a co-activator molecule, said co-activator molecule being operably linked to a promoter sequence; and b) contacting said host cell with an effective amount of an ecdysone ligand, thereby effecting increased expression of said gene of interest.

40. A method as claimed in the claim 39 wherein said first DNA construct encodes an altered insect ecdysone receptor, said second DNA construct encodes a receptor selected from the group consisting of insect ultraspiracle USP receptor and mammalian RXR receptor, said third construct comprising a promoter containing a plurality of ecdysone response elements, said promoter being operably linked to a gene of interest, said fourth construct encoding co-activator GRIP 1.

41. A method as claimed in the claim 39 wherein said first DNA construct encodes an altered insect ecdysone receptors, said second DNA construct encodes a receptor selected from the group consisting of an altered insect ultraspiracle USP receptor and mammalian RXR receptor, said third construct comprising a promoter containing a plurality of ecdysone response elements, said promoter being operably linked to a gene of interest, said fourth construct encoding a co-repressor, SMRT.

42. A method for identifying proteins which transactivate nuclear receptors in a ligand dependent manner, comprising:

a) providing a host cell containing:

(i) a first DNA construct having a nucleic acid molecule encoding an altered ecdysone receptor operably linked to a promoter, wherein said altered ecdysone receptor is an ecdysone receptor with a deleted A/B domain;

(ii) a second DNA construct having a nucleic acid molecule encoding a receptor which heterodimerizes with said altered ecdysone receptor upon transactivation, said nucleic acid molecule being operably linked to an promoter, wherein said receptor is selected from the group consisting of insect ultraspiracle gene product (USP) receptors and mammalian retinoid X receptors (RXR);

(iii) a third DNA construct comprising a promoter containing a plurality of ecdysone response elements, said promoter being operably linked to a reporter gene; and (iv) a fourth DNA construct encoding unknown protein molecule from a biological source, b) contacting said host cell with an effective amount of a ecdysone ligand; and c) assessing the level of ligand dependent co-activation by said protein as indicated by expression levels of said reporter gene.

43. A system as claimed in claim 1, wherein said and mammalian RXR is selected from the group consisting of retinoid X receptor α, retinoid X receptor β, and retinoid X receptor γ.

44. A method as claimed in claim 20, wherein said mammalian RXR is selected from the group consisting of retinoid X receptor α, retinoid X receptor β, and retinoid X receptor γ.

45. A method as claimed in claim 39, wherein said insect USP is selected from the group consisting of USP, USP a form, USP b form, and ΔA/B USP.

46. A method as claimed in claim 39, wherein said mammalian RXR is selected from the group consisting of retinoid X receptor β, retinoid X receptor β, and retinoid X receptor γ.

47. A method as claimed in claim 42, wherein said insect USP is selected from the group consisting of USP, USP a form, USP b form, and ΔA/B USP.

48. A method as claimed in claim 42, wherein said mammalian RXR is selected from the group consisting of retinoid X receptor α, retinoid X receptor β, and retinoid X receptor γ.

* * * * *